United States Patent
Levine et al.

(10) Patent No.: US 12,109,566 B2
(45) Date of Patent: Oct. 8, 2024

(54) CELL CONCENTRATION DEVICES AND METHODS INCLUDING A SYRINGE AND A SYRINGE HOLDER

(71) Applicant: Cervos Medical LLC, Marshfield, MA (US)

(72) Inventors: Andy H. Levine, Newton Highlands, MA (US); John C. Meade, Mendon, MA (US); Neil Tischler, Acton, MA (US); Jeffrey R. Chabot, Medford, MA (US); Andrew McGillicuddy, Humarock, MA (US); Neil F. Duffy, Jr., Brighton, MA (US)

(73) Assignee: Cervos Medical LLC, Avon, MA (US)

( * ) Notice: Subject to any disclaimer, the term of this patent is extended or adjusted under 35 U.S.C. 154(b) by 0 days.

(21) Appl. No.: 18/320,038

(22) Filed: May 18, 2023

(65) Prior Publication Data

US 2024/0123449 A1    Apr. 18, 2024

Related U.S. Application Data

(60) Continuation of application No. 17/715,222, filed on Apr. 7, 2022, now Pat. No. 11,660,603, which is a
(Continued)

(51) Int. Cl.
*B01L 3/00* (2006.01)
*A61M 1/02* (2006.01)
(Continued)

(52) U.S. Cl.
CPC ........... *B01L 3/5082* (2013.01); *A61M 1/029* (2013.01); *A61M 1/3693* (2013.01);
(Continued)

(58) Field of Classification Search
CPC .. B01L 3/5082; B01L 3/0282; B01L 3/50215; B01L 2200/026;
(Continued)

(56) References Cited

U.S. PATENT DOCUMENTS 3,814,248 A    6/1974  Lawhead
3,957,654 A    5/1976  Ayers
(Continued)

FOREIGN PATENT DOCUMENTS

CN    103657756 A    3/2014
EP    0493838 B1    7/1992
(Continued)

OTHER PUBLICATIONS

Notice of Allowance, U.S. Appl. No. 15/041,588, entitled, "Apparatus and Methods for Aspirating and Separating Components of Difference Densities from a Physiological Fluid Containing Cells," dated Mar. 1, 2018.
(Continued)

*Primary Examiner* — Walter D. Griffin
*Assistant Examiner* — Shuyi S. Liu
(74) *Attorney, Agent, or Firm* — Hamilton, Brook, Smith & Reynolds, P.C.

(57) ABSTRACT

A system and associated method for concentrating and separating components of different densities from fluid containing cells using a centrifuge includes a container defining a cavity for receiving the fluid. The container has a top, a sidewall extending from the top, and a bottom disposed opposite the top and in sealing engagement with the sidewall. An insert is slidably disposed in the cavity of the container and defines a lumen through the insert. The lumen, which includes a hole and a funnel-shaped upper portion in fluid communication with the hole, forms an open fluid path between opposite ends of the insert. The insert has
(Continued)

a density such that upon centrifugation a selected component of the fluid resides within the lumen. A container port is disposed in the top of the container to transfer the fluid into the container and to withdraw a fluid component other than the selected component from the container. The system includes a manifold that includes a manifold port, a vent to vent the container, and a connector to couple to the container port. A cannula is receivable in the manifold port and extendable through the container port into the container and into the lumen of the insert to withdraw the selected component from the lumen.

13 Claims, 15 Drawing Sheets

Related U.S. Application Data continuation of application No. 16/835,053, filed on Mar. 30, 2020, which is a division of application No. 14/764,115, filed as application No. PCT/US2014/013636 on Jan. 29, 2014, now Pat. No. 10,603,665.

(60) Provisional application No. 61/897,587, filed on Oct. 30, 2013, provisional application No. 61/757,993, filed on Jan. 29, 2013.

(51) Int. Cl.
A61M 1/36 (2006.01)
B01D 21/26 (2006.01)
B01L 3/02 (2006.01)

(52) U.S. Cl.
CPC .......... *B01D 21/262* (2013.01); *B01L 3/0282* (2013.01); *B01L 3/50215* (2013.01); *B01L 2200/026* (2013.01); *B01L 2200/0684* (2013.01); *B01L 2200/0689* (2013.01); *B01L 2300/046* (2013.01); *B01L 2300/0858* (2013.01); *B01L 2400/0409* (2013.01); *B01L 2400/0478* (2013.01)

(58) Field of Classification Search
CPC ..... B01L 2200/0684; B01L 2200/0689; B01L 2300/046; B01L 2300/0858; B01L 2400/0409; B01L 2400/0478; A61M 1/029; A61M 1/3693; B01D 21/262
See application file for complete search history.

(56) References Cited

U.S. PATENT DOCUMENTS

| | | |
|---|---|---|
| 4,001,122 A | 4/1977 | Griffin |
| 4,058,252 A | 11/1977 | Williams |
| 4,120,662 A | 10/1978 | Fosslien |
| 4,142,668 A | 3/1979 | Lee |
| 4,151,690 A | 5/1979 | Ballies |
| 4,152,270 A | 5/1979 | Cornell |
| 4,154,690 A | 5/1979 | Ballies |
| 4,443,345 A | 4/1984 | Wells |
| 4,809,860 A | 3/1989 | Allen |
| 4,818,418 A | 4/1989 | Saunders |
| 4,844,818 A | 7/1989 | Smith |
| 4,917,801 A | 4/1990 | Luderer et al. |
| 4,939,087 A | 7/1990 | Van Wie et al. |
| 5,030,341 A | 7/1991 | McEwen et al. |
| 5,053,134 A | 10/1991 | Luderer et al. |
| 5,236,604 A | 8/1993 | Fiehler |
| 5,269,927 A | 12/1993 | Fiehler |
| 5,271,852 A | 12/1993 | Luoma |
| 5,308,506 A | 5/1994 | McEwen et al. |
| 5,455,007 A | 10/1995 | Calvo et al. |
| 5,474,687 A | 12/1995 | Van Vlasselaer |
| 5,489,386 A | 2/1996 | Saunders |
| 5,555,920 A | 9/1996 | Godolphin et al. |
| 5,577,513 A | 11/1996 | Van Vlasselaer |
| 5,601,711 A | 2/1997 | Sklar et al. |
| 5,641,622 A | 6/1997 | Lake et al. |
| 5,707,331 A | 1/1998 | Wells et al. |
| 5,739,033 A | 4/1998 | Soon-Shiong |
| 5,840,502 A | 11/1998 | Van Vlasselaer |
| 6,051,146 A | 4/2000 | Green et al. |
| 6,123,655 A | 9/2000 | Fell |
| 6,221,315 B1 | 4/2001 | Giesler et al. |
| 6,410,334 B1 | 6/2002 | Schmolz |
| 6,516,953 B1 | 2/2003 | DiCesare et al. |
| 6,596,179 B2 | 7/2003 | Giesler et al. |
| 6,733,433 B1 | 5/2004 | Fell |
| 6,835,353 B2 | 12/2004 | Smith et al. |
| 7,077,273 B2 | 7/2006 | Ellsworth et al. |
| 7,179,391 B2 | 2/2007 | Leach et al. |
| 7,223,346 B2 | 5/2007 | Dorian et al. |
| 7,316,932 B2 | 1/2008 | Woodside |
| 7,374,678 B2 | 5/2008 | Leach et al. |
| 7,445,125 B2 | 11/2008 | Ellsworth et al. |
| 7,410,613 B2 | 12/2008 | Iwaki et al. |
| 7,547,272 B2 | 6/2009 | Ellsworth et al. |
| 7,514,075 B2 | 7/2009 | Hedrick et al. |
| 7,585,670 B2 | 9/2009 | Hedrick et al. |
| 7,595,043 B2 | 9/2009 | Hedrick et al. |
| 7,598,089 B2 | 10/2009 | Collins |
| 7,780,860 B2 | 8/2010 | Higgens et al. |
| 7,832,566 B2 | 11/2010 | Leach et al. |
| 7,845,499 B2 | 12/2010 | Higgens et al. |
| 7,914,689 B2 | 3/2011 | Higgens et al. |
| 7,954,646 B2 | 6/2011 | Leach et al. |
| 7,976,796 B1 | 7/2011 | Smith et al. |
| 7,992,725 B2 | 8/2011 | Leach et al. |
| 8,048,321 B2 | 11/2011 | Leach et al. |
| 8,048,678 B2 | 11/2011 | Duffy, Jr. et al. |
| 8,062,534 B2 | 11/2011 | Higgens et al. |
| RE43,547 E | 7/2012 | Ellsworth et al. |
| 8,241,592 B2 | 8/2012 | Duffy et al. |
| 9,272,083 B2 | 3/2016 | Duffy |
| 9,421,319 B2 | 8/2016 | Hwang |
| 10,005,081 B2 | 6/2018 | Duffy et al. |
| 10,603,665 B2 | 3/2020 | Levine et al. |
| 11,660,603 B2 | 5/2023 | Levine et al. |
| 2002/0006360 A1 | 1/2002 | Neal et al. |
| 2003/0205538 A1 | 11/2003 | Dorian et al. |
| 2004/0256331 A1 | 12/2004 | Arking et al. |
| 2005/0109716 A1 | 5/2005 | Leach et al. |
| 2005/0124073 A1 | 6/2005 | Freund |
| 2005/0274679 A1 | 12/2005 | Kao et al. |
| 2006/0178644 A1 | 8/2006 | Reynolds |
| 2006/0196885 A1 | 9/2006 | Leach et al. |
| 2006/0273049 A1 | 12/2006 | Leach et al. |
| 2006/0273050 A1 | 12/2006 | Higgens et al. |
| 2006/0278588 A1 | 12/2006 | Woodell-May |
| 2007/0032775 A1 | 2/2007 | Niedospial et al. |
| 2007/0088252 A1 | 4/2007 | Pestotnik et al. |
| 2007/0131612 A1 | 6/2007 | Duffy et al. |
| 2007/0265558 A1 | 11/2007 | Kleinbloeseum et al. |
| 2008/0171951 A1 | 7/2008 | Fell |
| 2009/0186065 A1 | 7/2009 | Tillman et al. |
| 2009/0283524 A1 | 11/2009 | Ellsworth et al. |
| 2010/0140182 A1 | 6/2010 | Chapman et al. |
| 2010/0256595 A1 | 10/2010 | Leach et al. |
| 2011/0056893 A1 | 3/2011 | Leach et al. |
| 2011/0086426 A1 | 4/2011 | Freund |
| 2011/0124106 A1 | 5/2011 | Froman |
| 2011/0168193 A1 | 7/2011 | Leach et al. |
| 2012/0015796 A1 | 1/2012 | Leach et al. |
| 2012/0052577 A1 | 3/2012 | Espinosa et al. |
| 2012/0082652 A1 | 4/2012 | Sengun et al. |
| 2012/0129676 A1 | 5/2012 | Duffy et al. |
| 2013/0079212 A1 | 3/2013 | Ellsworth et al. |
| 2014/0148325 A1 | 5/2014 | Jo et al. |
| 2014/0227732 A1 | 8/2014 | Saqi et al. |
| 2015/0004079 A1 | 1/2015 | Hassouneh et al. |
| 2015/0064687 A1 | 3/2015 | Nemirovsky |

(56) References Cited

U.S. PATENT DOCUMENTS

| | | |
|---|---|---|
| 2015/0367064 A1 | 12/2015 | Pennie |
| 2016/0008808 A1 | 1/2016 | Levine et al. |
| 2016/0158716 A1 | 6/2016 | Vos et al. |
| 2016/0263571 A1 | 9/2016 | Duffy et al. |
| 2020/0324285 A1 | 10/2020 | Levine et al. |
| 2020/0360921 A1 | 11/2020 | McGillicuddy |
| 2022/0226812 A1 | 7/2022 | Levine et al. |

FOREIGN PATENT DOCUMENTS

| | | |
|---|---|---|
| EP | 1289618 B1 | 4/2001 |
| EP | 2407245 A2 | 1/2012 |
| KR | 10-1333789 B1 | 11/2013 |
| KR | 10-2014-0004890 A | 1/2014 |
| KR | 20-0471024 Y1 | 1/2014 |
| KR | 10-2014-0017948 A | 2/2014 |
| WO | 200183068 A1 | 11/2001 |
| WO | 2002098566 A2 | 12/2002 |
| WO | 2003099412 A1 | 12/2003 |
| WO | 2005039773 A1 | 6/2005 |
| WO | 2007050986 A1 | 3/2007 |
| WO | 2010058806 A1 | 5/2010 |
| WO | 2010138895 A2 | 12/2010 |
| WO | 2014036945 A1 | 3/2014 |
| WO | 2014120797 A1 | 8/2014 |
| WO | 2019108937 A1 | 6/2019 |

OTHER PUBLICATIONS

Non-Final Office Action, U.S. Appl. No. 15/041,588, entitled, "Apparatus and Methods for Aspirating and Separating Components of Difference Densities from a Pysiological Fluid Containing Cells," dated Mar. 1, 2018, date of mailing: Sep. 26, 2017.
"GPS III Platelet Separation System", Biomet Biologics, (8 pages), Jul. 15, 2007.
"RES-Q60 BMC Bone marrow concentrate", retrieved on May 4, 2010 from Thermogenesis Website URL: http://www.thermogenesis.com/CMSFiles/Pdf/Literature/resqbmc.pdf.
International Preliminary Report on Patentability from International Application No. PCT/US2010/036696, entitled "Apparatus and Methods for Aspirating and Separating Components of Different Densities From a Physiological Fluid Containing Cells", dated Dec. 8, 2011.
International Preliminary Report on Patentability from International Application No. PCT/US2014/013636, entitled "Cell Concentration Devices and Methods", dated Aug. 4, 2015.
International Search Report and Written Opinion of the International Searching Authority from International Application No. PCT/US2014/013636, entitled "Cell Concentration Devices and Methods," dated Jun. 4, 2014.
Joupperi, et al., "Isolation of Bone Marrow-Derived Stem Cells Using Density-Gradient Separation", Exp. Hematol, 35(2): 335-341 (Feb. 2007).
Zhang, et al., "Isolating and Culturing Rat Marrow Mesenchymal Stem Cells and Studying their Phenotypical and Functional Properties", Sichuan Da Xue Xue Bao Yi Xue Ban. 34(4): 738-741 (Oct. 2003). Abstract Only.
Office Action, U.S. Appl. No. 13/322,616, entitled "Apparatus and Methods for Aspirating and Separating Components of Different Densities From a Physiological Fluid Containing Cells," dated Apr. 3, 2015.
Notice of Allowance, U.S. Appl. No. 13/322,616, entitled, "Apparatus and Methods for Aspirating and Separating Components of Different Densities from a Physiological Fluid Containing Cells," dated Oct. 27, 2015.
International Search Report and the Written Opinion of the International Searching Authority from International Application No. PCT/US2010/036696, entitled "Apparatus and Methods for Aspirating and Separating Components of Different Densities From a Physiological Fluid Containing Cells," dated Aug. 18, 2011.
"RES-Q60 BMC Point-of-Care Automated Cell Capturing System", retrieved Apr. 2010 from TotipotentSC Corporate Website URL: http://totipotentsc.com/products/RES-Q60M_V2.pdf.
NonFinal Office Action, U.S. Appl. No. 14/764,115 entitled: "Cell Concentration Devices and Methods," dated Mar. 9, 2018.
Final Office Action, U.S. Appl. No. 13/322,616, entitled "Apparatus and Methods for Aspirating and Separating Components of Different Densities From a Physiological Fluid Containing Cells," dated Jul. 30, 2015.
Duregger et al., "Influence of storage conditions on the release of growth factors in platelet-rich blood derivatives," Current Directions in Biomedical Engineering, vol. 2, No. 1, pp. 311-314, (2016).
International Search Report and the Written Opinion of the International Searching Authority from International Application No. PCT/US2018/063317, entitled "Apparatus and Method for Centrifuging a Biologic," mailed Feb. 4, 2019.
International Preliminary Report on Patentability for International Application No. PCT/2018/063317, entitled "Apparatus and Method for Centrifuging a Biologic," dated Jun. 2, 2020.
Non-Final Office Action for U.S. Appl. No. 16/767,863, entitled "Apparatus and Method for Centrifuging a Biologic," dated Mar. 17, 2022.
Non-Final Office Action for U.S. Appl. No. 16/835,053, entitled "Cell Concentration Devices and Methods That Include an Insert Defining a Lumen and a Cannula Assembly," dated Nov. 2, 2022.
Non-Final Office Action for U.S. Appl. No. 17/715,222, consisting of 21 pages, dated Jun. 6, 2022.
Non-Final Office Action for U.S. Appl. No. 17/715,222, consisting of 11 pages, dated Jan. 10, 2023.
Interview Summary for U.S. Appl. No. 17/715,222, consisting of 3 pages, dated Jan. 31, 2023.
Notice of Allowance for U.S. Appl. No. 17/715,222, consisting of 11 pages, dated Mar. 3, 2023.
Final Office Action for U.S. Appl. No. 16/835,053, entitled "Cell Concentration Devices and Methods That Include an Insert Defining a Lumen and a Cannula Assembly," dated Jun. 15, 2023.
Notice of Allowance for U.S. Appl. No. 16/835,053, entitled "Cell Concentration Devices and Methods That Include an Insert Defining a Lumen and a Cannula Assembly," dated Nov. 1, 2023.
Final Office Action for U.S. Appl. No. 16/835,053, "Cell Concentration Devices and Methods That Include an Insert Defining a Lumen and a Cannula Assembly" dated: Jul. 22, 2024.

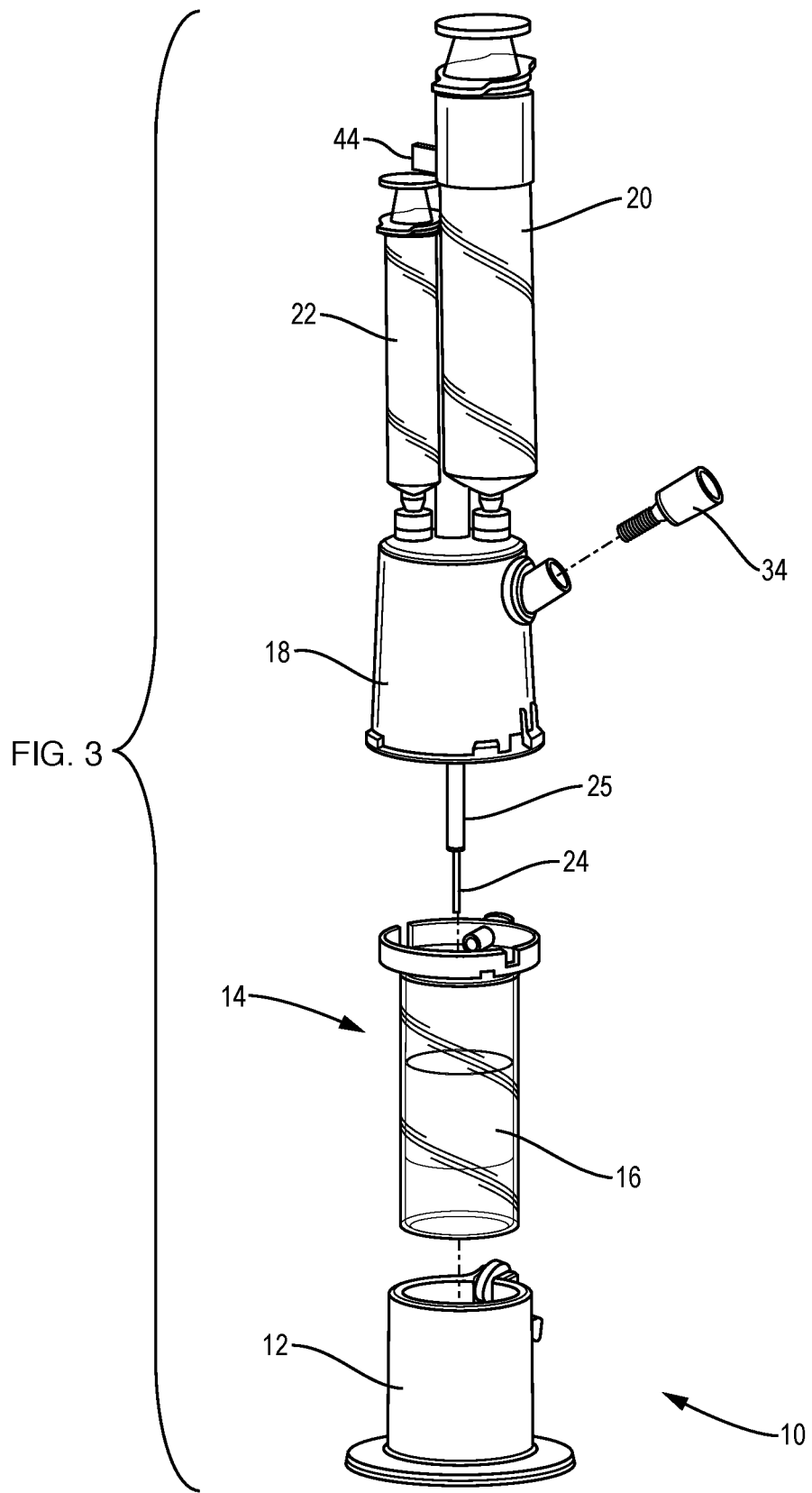

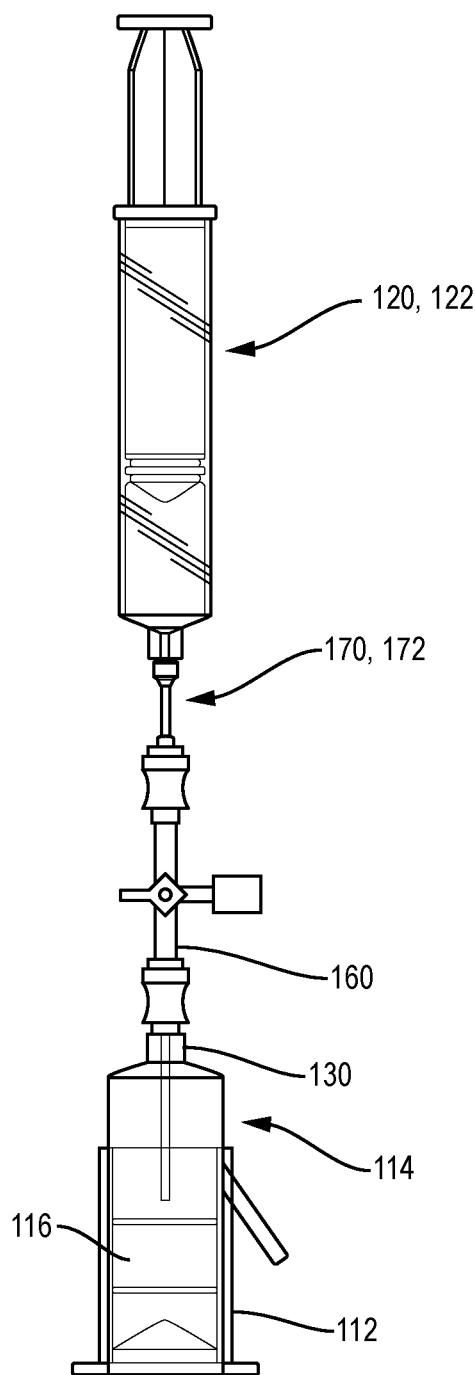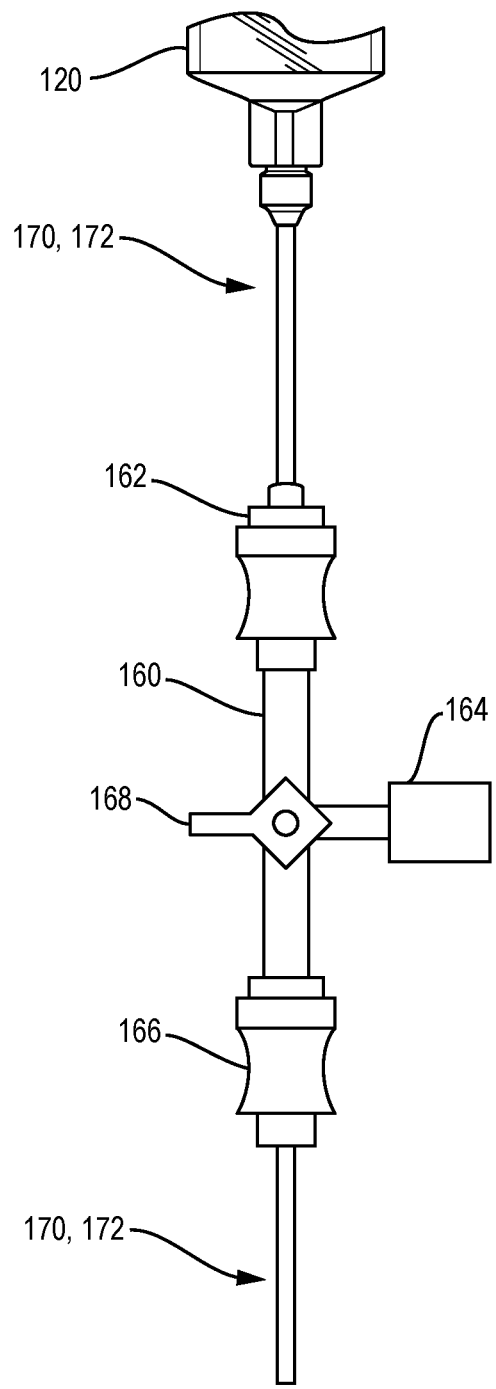
FIG. 14A
FIG. 14B

CELL CONCENTRATION DEVICES AND METHODS INCLUDING A SYRINGE AND A SYRINGE HOLDER

RELATED APPLICATIONS

This application is a continuation of U.S. application Ser. No. 17/715,222, filed on Apr. 7, 2022, which is a continuation of U.S. application Ser. No. 16/835,053, filed on Mar. 30, 2020, which is a divisional of U.S. application Ser. No. 14/764,115, filed Jul. 28, 2015, now U.S. Pat. No. 10,603,665, which is the U.S. National Stage of International Application No. PCT/US2014/013636, filed on Jan. 29, 2014, published in English, which claims the benefit of U.S. Provisional Application No. 61/757,993, filed on Jan. 29, 2013 and U.S. Provisional Application No. 61/897,587, filed on Oct. 30, 2013. The entire teachings of the above applications are incorporated herein by reference.

BACKGROUND OF THE INVENTION

In the field of regenerative medicine, access to a broad cross section of sub-dermal tissue is typically required to not only source cells but to also deliver therapy. Fluid tissue that is aspirated or otherwise sourced is often separated into one or more components that are present in the fluid tissue, e.g., plasma, red blood cells, fat cells, stem cells or other nucleated cells. Typically, one or more selected components of the fluid tissue are concentrated into a small volume so that the selected components can be used clinically. For example, there are several commercial devices to separate and concentrate nucleated cells from aspirated bone marrow, fat, or cord blood. Some of these systems employ a floating insert or buoy that is meant to create an interface between the separated fluid components or fractions of interest. The challenge for any apparatus designed to accomplish such a task is the ability to volume reduce the fluid in which the nucleated cells are suspended while recovering as many cells as possible. For example, in marrow aspirate, approximately 1 to 2 percent of the cells suspended in the fluid are the target nucleated cells. Many commercial devices are not able to consistently capture high percentages of nucleated cells while at the same time efficiently volume reduce (i.e., concentrate) the beginning fluid. In other words, many devices are not able to simultaneously obtain a high yield and a high final concentration.

Apparatus and methods for separating components of different densities from a physiological fluid containing cells are described in a previously filed application, International Application No. PCT/US2010/036696, filed on May 28, 2010, published on Dec. 2, 2010 as WO 2010/138895 A2, and incorporated herein by reference in its entirety.

FIG. 1 is a diagram illustrating a separation system 1700 showing different components of a fluid inside the container 1702 after centrifugation. After centrifugation, the least dense fluid 2000 will be above the insert 1300. The insert can be made of a material of a certain density such that after centrifugation of blood, including blood from marrow, the insert spans the space between the least dense plasma 2000 and the dense red cells 2004, with the intermediate dense material 2002, e.g., nucleated cells, residing in the upper funnel-shaped portion 1304 of the insert. The separation system 1700 can include a vent 1716 disposed in the top 1706 of the container 1702 and a fluid port 1718 disposed in or adjacent the top 1706. The air vent 1716 can prevent a vacuum from being created when fluid is withdrawn from the container 1702. A cannula assembly 1500 with a closed end 1502 is inserted through the injection port 1714. Before insertion of the cannula assembly, a clamp 1800 can be applied to sidewall of container 1702 to hold the insert 1300 in place during subsequent fluid extraction. The closed end 1502 of the cannula assembly butts against the insert and closes the through hole 1308 of the insert. The closed end of the cannula assembly 1500 and the insert can form a seal, thus isolating denser fluid component or components beneath the seal from fluid components above the seal. The cannula assembly includes two cannulae, an inner cannula 1508 and an outer cannula 1510, that fit coaxially into each other.

As shown in FIG. 1, the cannula assembly includes a series of two parallel side holes or ports in the two cannulae to line up at different predetermined heights above the closed distal end 1502. A first set of side ports 1506 can be located near the closed distal end 1502. A second set of side ports 1504 can be located above the upper funnel-shaped portion 1304 of insert 1300. Fluid above the distal end 1502 of the cannula assembly can be removed in at least two fractions or components based on these two different predetermined heights. Fluid can be removed through the cannula assembly 1500 into connected syringes 1802, 1804 using valve 1806. For example, when the top side ports 1504 are aligned and opened, fluid above the top side ports can be extracted into a first syringe 1802 through inner cannula 1508. By rotating the two cannulae with respect to each other, the top side ports in the cannula assembly 1500 are misaligned and sealed off, while the bottom side ports are aligned and opened. As shown in FIG. 1, the side ports may be radially offset by 90 degrees, requiring a relative rotation of 90 degrees to change which ports are aligned. When the bottom side ports 1506 are located just above the seal created by the closed end 1502 of the cannula assembly, substantially all fluid above the seal, but below the top side ports, can be extracted through inner cannula 1508 into a second syringe 1804.

FIGS. 2A-2C are a series of sequential diagrams illustrating the extraction of fluid components using a separation system 2100, the system including a container 2102 having a movable bottom or plunger 2104. Centrifugation separates the fluid in the container by density into separate components or fractions. FIG. 2A illustrates the position of an insert, such as insert 2600, in relation to three components of a fluid in the separation system 2100 after centrifugation. The components are a low density fraction 2000, such as plasma, a medium density fraction 2002, such as buffy coat or nucleated cells, and a high density fraction 2004, such as red blood cells.

To retrieve the separated layers or fluid components, the user takes the syringe or container 2102 out of the centrifuge. As shown in FIGS. 2A-2B, the user then uncaps the luer connector of port 2118, attaches a plasma extraction syringe 2300, and pulls back on the plunger. The calculated combination of 1) the fluid flow of plasma as it is being evacuated from the collection syringe or container 2102, which can be lateral to the center injection port, 2) the size of the center hole 2608 or holes 2610 in the insert 2600, 3) the relative density of the different fluids inside the container 2102, and 4) the forces required to extract fluid of different densities under these known parameters, results in substantially only plasma moving into the plasma syringe 2300. Because the air vent 2116 is capped, the collection syringe or container 2102 is a vacuum. Thus the movable bottom or plunger 2104 and the insert 2600 rise in the collection syringe or container 2102 as the plasma is extracted. The target cells, such as buffy coat, stay in the through hole or holes 2610 of the insert 2600.

As shown in FIGS. 2B-2C, after removal of the plasma 2000, the insert 2600 has risen to the top of the syringe or container 2102 and effectively seals off port 2118 connected to the plasma extraction syringe. At this point the user uncaps the air vent 2116 making the collection syringe or container 2102 no longer under vacuum pressure. A second target cell extraction syringe 2302 with a cannula 2400 attached is then inserted through the center injection port 2114. Since 1) the insert 2600 always ends up at the top of the collection syringe or container 2102 after removal of the plasma and 2) the height of the insert 2600 is known, then the distance between the top of the injection port 2114 and bottom of the through holes 2610, 2608 of the insert 2600 is always the same after removal of the plasma. The length of the cannula 2400 is such that it reaches just to the bottom of the center through hole 2608 in the insert 2600 after removal of the plasma. Thus, when the user pulls back on the plunger of the target cell extraction syringe 2302, after the air vent 2116 has been uncapped, the target cells residing in the through hole or holes 2610, 2608 are removed.

SUMMARY OF THE INVENTION

A system for separating components of different densities from a physiological fluid containing cells using a centrifuge includes a container having a top, a sidewall extending from the top, and a bottom disposed opposite the top and in sealing engagement with the sidewall. The container defines a cavity for receiving the fluid. The system includes an insert slidably disposed in the cavity of the container. The insert defines a lumen through the insert, the lumen including a hole and a funnel-shaped upper portion in fluid communication with the hole. The lumen forms an open fluid path between opposite ends of the insert. The insert has a density such that upon centrifugation a selected component of the fluid resides within the lumen. A container port is disposed in the top of the container to transfer the fluid into the container and to withdraw a fluid component other than the selected component from the container. The system further includes a manifold that includes a manifold port, a vent to vent the container, and a connector to couple to the container port. A cannula is receivable in the manifold port and extendable through the container port into the container and into the lumen of the insert to withdraw the selected component from the lumen.

The cannula can include a closed end to close the hole in the insert and a side port to withdraw the selected component. The cannula and the insert may form a seal when the closed end of the cannula closes off the hole in the insert. In an embodiment, the cannula a first cannula, and the system further includes a second cannula extendable through the container port to withdraw the component other than the selected component. The second cannula may be receivable in the manifold port. The system may include two manifolds, each including a manifold port, a vent to vent the container, and a connector to couple to the container port, and the first cannula can be receivable in the manifold port of one manifold while the second cannula can be receivable in the manifold port of the other manifold.

The container can be a syringe and the bottom can be movable, i.e., a plunger, which can have a removable handle. In an embodiment, the plunger is a first plunger and the system further includes a second plunger disposed in the syringe below the first plunger to move the first plunger, for example, to transfer the fluid into the container. The system may further include a clamping mechanism to hold the insert in place after centrifugation, the clamping mechanism being configured to press the sidewall of the container inward against the insert.

A method of separating components of different densities from a fluid containing cells using a centrifuge includes receiving the fluid in a separation system such as the separation system described above, and applying centrifugal force to the separation system. The method further includes, after centrifugation, withdrawing a fluid component other than the selected component through the container port; coupling a manifold to the container port, the manifold including a manifold port and a vent to vent the container; extending a cannula through the container port into the container and into the lumen of the insert, the cannula receivable in the manifold port; and withdrawing the selected component with the cannula from the lumen of the insert.

Withdrawing the selected component may include withdrawing the selected component through a side port in the cannula. In an embodiment, the cannula is a first cannula and withdrawing the component other than the selected component includes extending a second cannula through the container port, the second cannula receivable in the manifold port, and withdrawing the component other than the selected component with the second cannula. The manifold can be coupled to the container before the withdrawing of the component other than selected component. The method may further include with a clamping mechanism, holding the insert in place after centrifugation.

A system for separating components of different densities from a physiological fluid containing cells using a centrifuge includes a container, having a bottom, a top disposed opposite the bottom, and a sidewall extending from the top, the container defining a cavity for receiving the fluid. An insert is slidably disposed in the cavity and defines a lumen through the insert, the lumen including a hole and a funnel-shaped upper portion in fluid communication with the hole. The insert has a density such that upon centrifugation a selected component of the fluid resides within the lumen. The lumen forms an open fluid path between opposite ends of the insert. A container port is disposed in the top of the container. An extraction cap is provided to couple to the top of the container, the extraction cap including a cannula assembly receivable in the container port. The cannula assembly is extendable into the cavity of the container to butt against the insert and to withdraw the selected component from the lumen of the insert.

The cannula assembly can include an inner cannula coaxially disposed within an outer cannula. The inner cannula may include a closed end to close the hole in the insert and a side port to withdraw the selected component, the inner cannula and the insert forming a seal when the closed end of the inner cannula closes off the hole in the insert. The outer cannula may include an open end displaced from the distal end of the cannula assembly to withdraw fluid at a predetermined height above the distal end of the cannula assembly.

In an embodiment, the extraction cap includes a first port in fluid communication with the inner cannula and a second port in fluid communication with the outer cannula. The system may further include a first syringe to couple to the first port and a second syringe to couple to the second port. The cap may include an assembly tab adjacent the first and second ports, the assembly tab extending from the cap to prevent the second syringe from coupling to the first port. The system may further include a lock-out element on the second syringe. For example, the lock-out element includes a tab that locks a plunger of the first syringe until second syringe is removed from the cap. In an embodiment, the extraction cap includes an outer part and an inner part, the inner part carrying the needle assembly and being movable relative to the outer part. The cap may include a locking screw coupled to the outer part and positioned at an angle relative to inner part to push the inner part toward the container with rotation of the locking screw.

A method of separating components of different densities from a fluid containing cells using a centrifuge includes receiving the fluid in a separation system, the system including a container having a bottom, a top disposed opposite the bottom, and a sidewall extending from the top, the container defining a cavity for receiving the fluid. A container port is disposed in the top of the container. An insert is slidably disposed in the cavity of the container, the insert including a funnel-shaped upper portion and a hole therethrough, the insert having a density such that upon centrifugation a selected component of the fluid resides within the upper portion of the insert. The method includes applying centrifugal force to the system and inserting a cannula into the container through the container port to butt against the insert, the cannula having one or more side ports displaced from a distal end of the cannula. The method further includes withdrawing the selected component through the side ports in the cannula; ejecting at least a portion of the withdrawn component through the side ports causing one or more fluid jets in the funnel-shape upper portion of the insert to release cells that adhere to the insert; and withdrawing the ejected portion and cells released by the fluid jets through the side ports.

In any of the systems or methods described herein the insert can be rigid. The volume contained in the lumen upper portion of the insert can be between 5% and 20% of the volume of the container cavity. The selected component (also referred to herein as a target fraction) can be buffy coat and the component other than the selected component can be blood plasma.

Embodiments of the current invention overcome the limitations of known devices for concentration of cells sourced from marrow or other tissue. For example, the insert of the separation device does not form a closed recess or a depression or indent to capture cells, but rather allows for the natural sedimentation of the fluid within the container and through the insert. The insert defines a lumen that has at least one relatively large through hole or channel, including a funnel-shaped upper portion, that allows for the free flow of fluid within the container and through the insert and does not interfere with the natural layering of different density components of the fluid. In addition, the insert identifies the location of a layer of interest, including the target cells. The funnel-shaped upper portion and the through hole reduce the cross-sectional area and increase the thickness of the layer of interest. This facilitates extraction of the target cells and contributes to a high yield and high concentration of the target cells.

Embodiments of the current invention overcome limitations of other systems that use inserts or buoys without a through hole and where the fluid path under centrifugation is confined to the distance between the inner wall of a container or tube and the outer walls of the inserts or buoys. In those systems, minor clots, particles, or other inconsistencies in the fluid can lodge between the walls of the tube and the buoys interfering with the natural layering of the different density components of the fluid. The insert(s) described includes a density selected such that after centrifugation the target cells reside within the hole, the funnel-shape upper portion, or lumen defined by the insert. Under gravitational force the insert floats freely within the container with substantially all of the fluid flowing through the hole or lumen of the insert, but not between the outer wall of the insert and the inner wall of the container. The distance between the inner wall of the container and the outer wall of the insert creates enough space to allow the insert to move freely within the container.

Embodiments of apparatus and methods for separating components of a fluid can be combined with devices and methods to access and source, e.g., aspirate, tissue, such as the aspiration needle assemblies described in International Application No. PCT/US2010/036696. Once tissue is sourced, e.g., loaded into a separation system, the system can be centrifuged. Upon centrifugation, the target cells naturally sediment into the through hole or lumen of the floating insert. These cells are then isolated by means of a cannula. The closed end of the cannula can close the hole in the insert. The target cells residing in the hole of lumen of the floating insert may be sealed from fluid below while fluid above the insert is removed through a cannula. The combination of the cell concentration and separation apparatus described herein with an aspiration apparatus allows a clinician the ability to access subcutaneous tissue in a less traumatic manner and then concentrate nucleated cells from that tissue aspirate. The apparatus can be combined, e.g., coupled or connected, by means of tubing and fluid ports, including luer connections, to create a total solution from aspiration to concentration.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3 is an exploded view of a system for separating components of difference densities from a physiological fluid according to an example embodiment of the invention.

FIG. 14A illustrates elements of the system of FIG. 10A arranged for extraction of fluid components from the container.

FIG. 14B is a detailed view of the cannula and manifold of FIG. 14A.

DETAILED DESCRIPTION OF THE INVENTION

Figure 1:
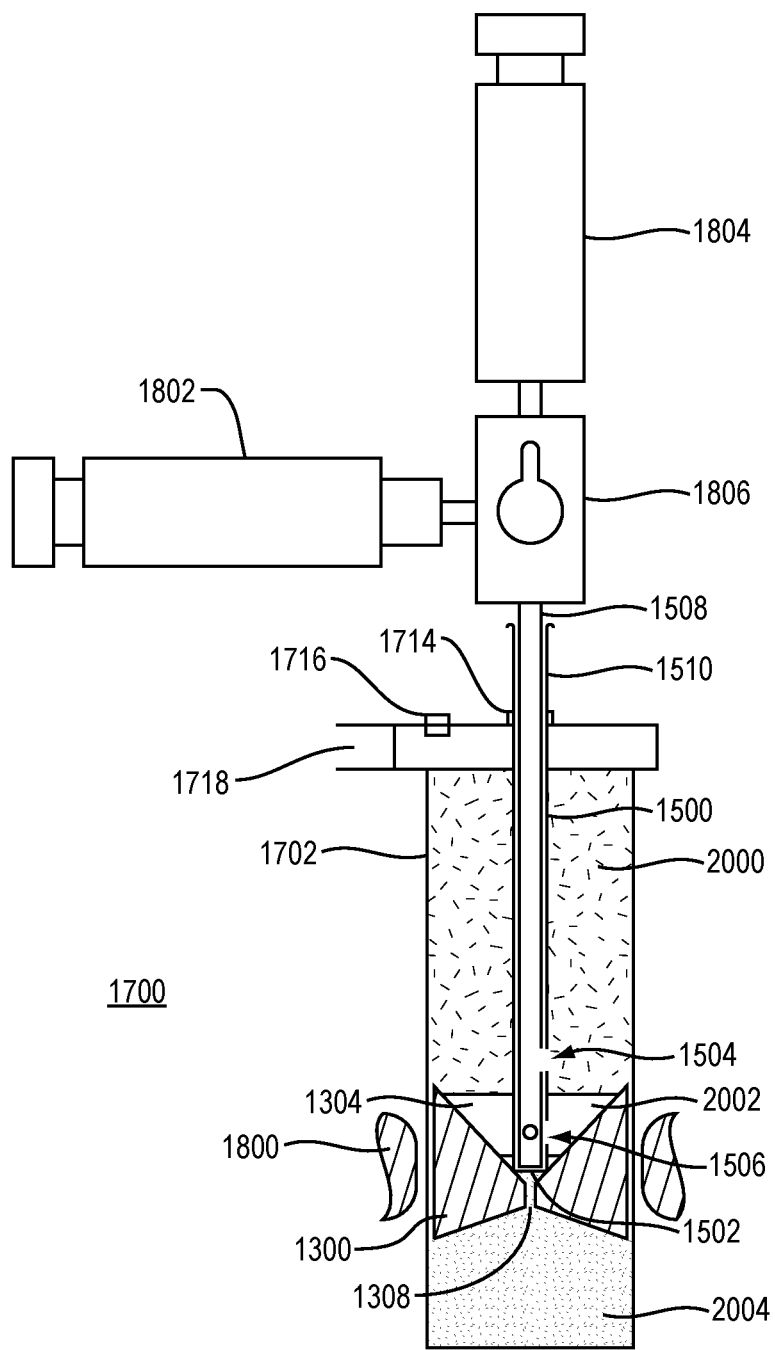
FIG. 1 illustrates a separation system showing different components of a fluid after centrifugation.

A description of example embodiments of the invention follows.

A prior version of a system for concentrating and separating cells (also referred to herein as a cell concentrator) has been described in International Application No. PCT/US2010/036696, published on Dec. 2, 2010 as WO2010/138895, incorporated herein by reference in its entirety. Here, an improved system is described that has been fabricated and tested. Some key features of the improved system include:
 a) a locking base;
 b) a double needle extraction system with jet flushing;
 c) an extraction needle lock that forces needle to seat in float; and
 d) a syringe lock-out tab to ensure proper order of extraction.

FIG. 3 is an exploded view of an improved system 10 for separating components of difference densities from a physiological fluid according to an example embodiment of the invention. System 10 includes a base 12, a separation vial (container) 14, a float (insert) 16 disposed in the vial 14, and an extraction cap 18 with syringes 20, 22 and a cannula assembly including extraction needles (cannulae) 24, 25.

To separate buffy coat from red blood cells and plasma, the float 16 should have a density that matches that of the buffy coat, whose density is roughly 1.06 g/cc. A polystyrene material was selected to manufacture the insert because the material's density is close to that of buffy coat. However, testing indicated that a polystyrene float was lighter than desired. Small slugs 56 (FIG. 9), e.g., pieces of stainless steel, can be added into the float to adjust its density. The process of testing a device in blood to ensure that the density matches the desired density can be repeated for new batches of plastic, e.g., during manufacturing, or for testing different materials.

The materials of the system are polycarbonate for most of the parts with the vial being PET (Polyethylene teraphthalate plastic) and the float polystyrene, as described above. Other suitable materials for the float may be polyethylene or polypropylene materials which tend to be less sticky to cells than polystyrenes. However, the densities of these materials are lower than that of buffy coat, so a larger metal material may need to be incorporated into the float to achieve the desired density. Another option is to coat the surface of the float and the inside of the vial with a substance that prevents cells form sticking, for example, a coating from the company Hydromer.

Figure 4:
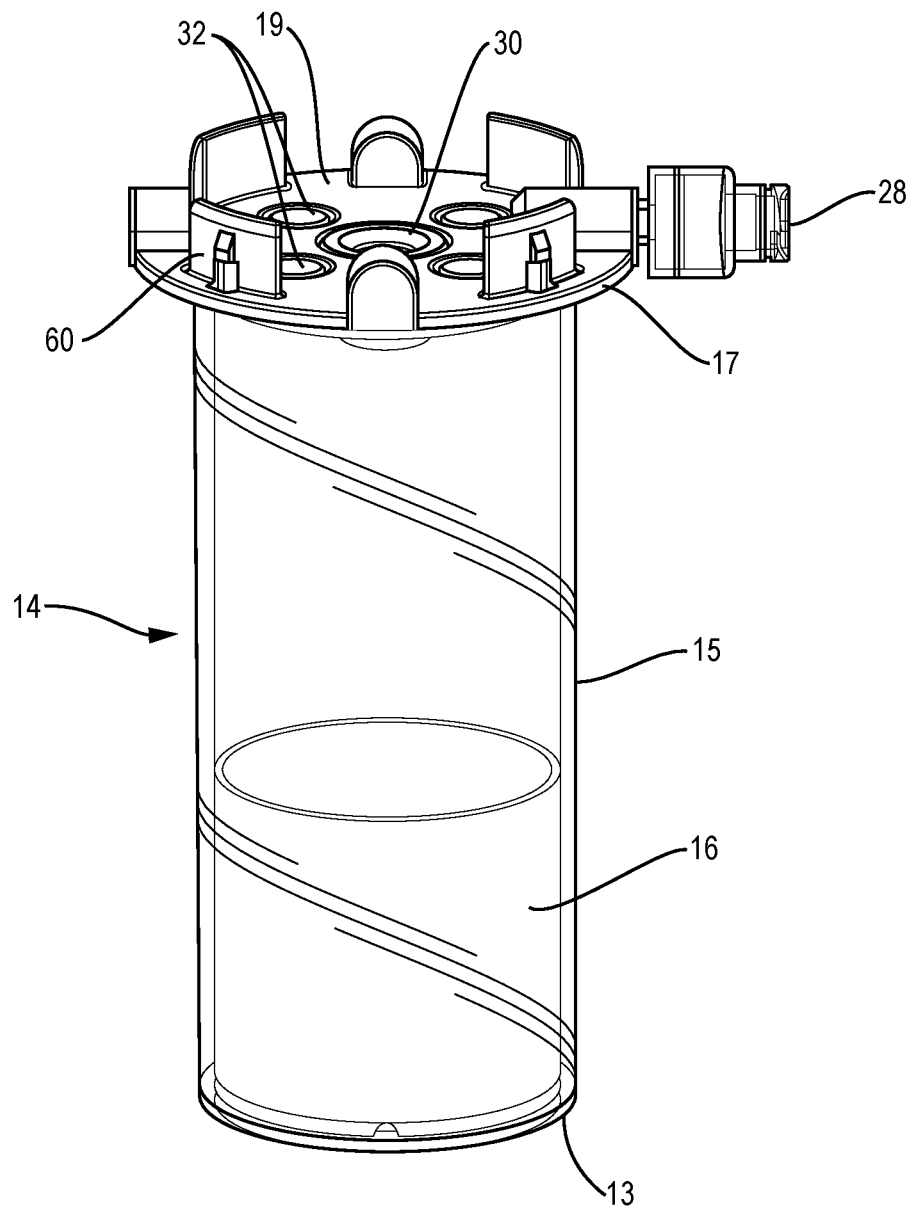
FIG. 4 is a perspective view of a container including an insert according to an example embodiment of the invention.
Figure 5:
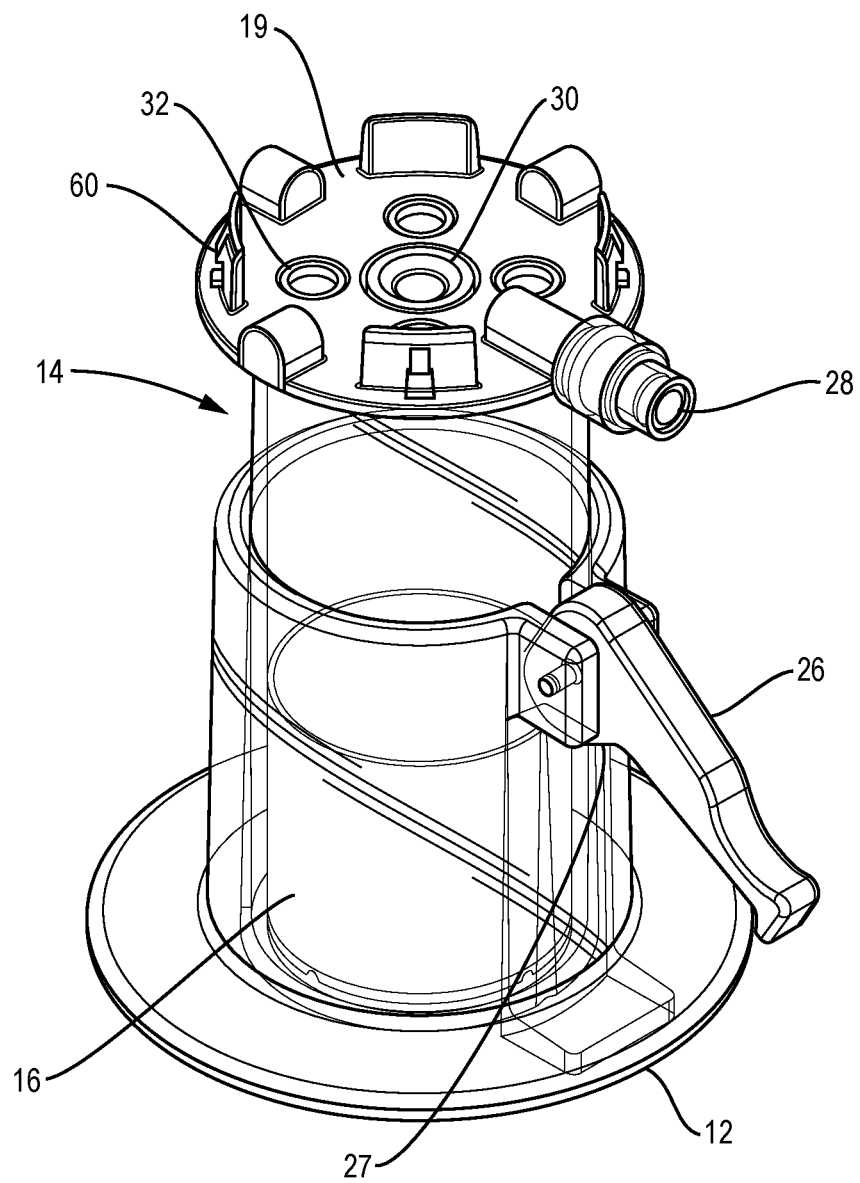
FIG. 5 is a perspective view of the container of FIG. 3 positioned in a base including a clamping mechanism.

FIG. 4 is a perspective view of container 14 including an insert 16 according to an example embodiment of the invention. Container 14 is a vial that has a bottom 13, a top 17 disposed opposite the bottom, and a sidewall extending from the top, the top including a lid 19 to close the container. The vial defines a cavity for receiving fluid. A physiological fluid containing cells, such as blood or marrow, is introduced into the separation vial 14 via a port 28 prior to centrifugation. After the fluid is centrifuged, the separation vial 14 is placed into the base 12. As shown in FIG. 5, the base 12 has a lever 26 with a cam 27 that locks the vial to the base by deforming the vial wall 15. This deformation locks the float 16 inside the vial 14 in place so that it cannot move. In other words, the cam and lever of base 12 operate as a clamping mechanism that, when engaged, prevents movement of the float. Movement of the float, such as during the extraction procedures described below, can disrupt the target cell layer, e.g., the buffy coat.

Post centrifugation, the serum (plasma) is above the float 16, the red blood cells are below the float and the target cells (e.g., buffy coat) are inside the float funnel. This separation of fluid components is analogous to what is shown in FIG. 1. The cap or lid 19 of the vial 14 includes a silicone septum 30 and air vents 32. As shown in FIGS. 4 and 5, four air vents 32 are arranged around the septum 30 and four protrusions 60 extend from the lid 19. The extraction needles (cannulae) 24, 25 are inserted through the septum 30, which functions as a port into the container. The air vents are included so that one does not pull a vacuum when extracting the target cells or the plasma serum.

Figure 6:
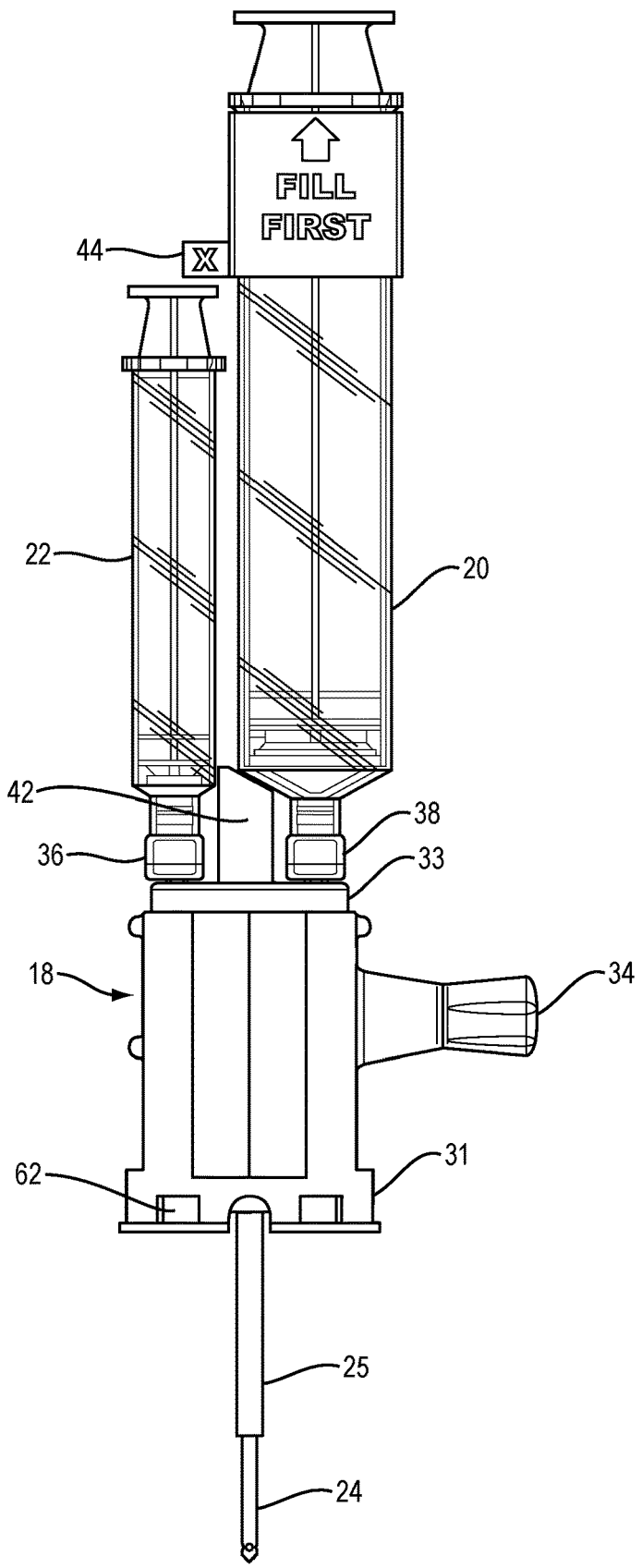
FIG. 6 is a side view of an extraction cap according to an example embodiment of the invention.

FIG. 6 is a side view of an extraction cap 18 according to an example embodiment of the invention. Extraction cap 18 is distinct from the lid 19 configured to couple to the top of the vial (container) 14. The extraction cap includes the cannula assembly, including needles (cannulae) 24 and 25, which are receivable in container port 30.

Figure 7:
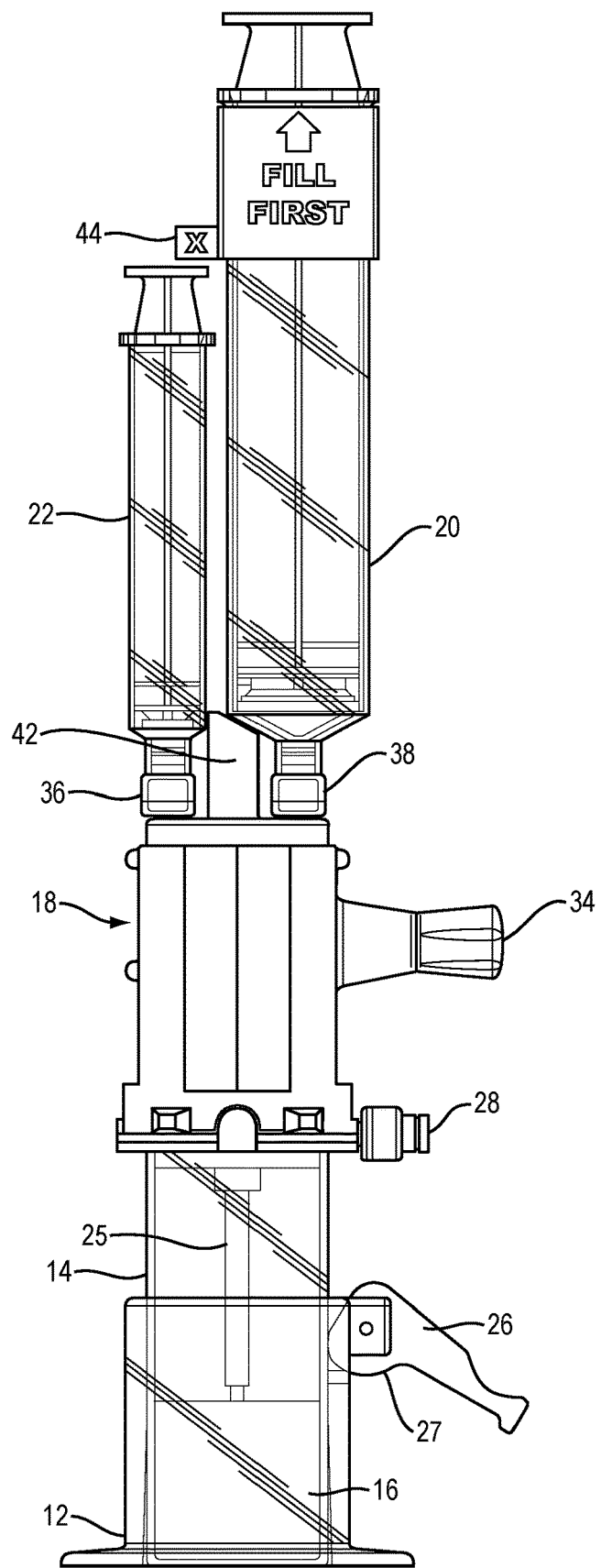
FIG. 7 is a side view of a system including the container and base of FIG. 5 and the extraction cap of FIG. 5.
Figure 8:
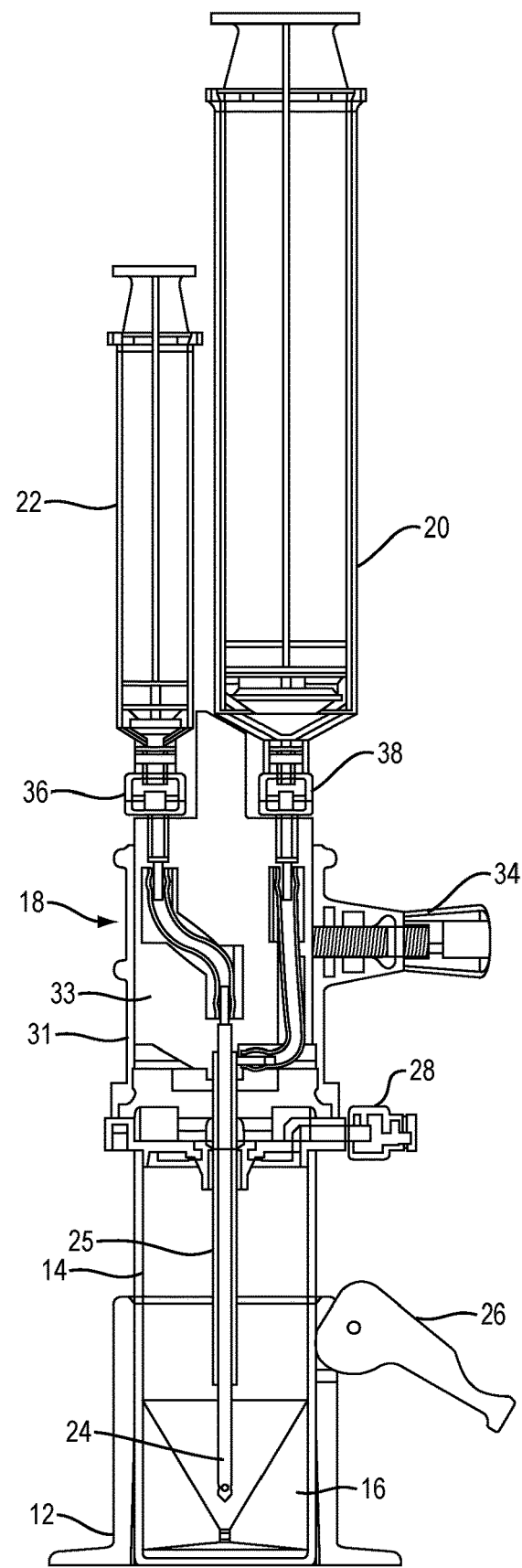
FIG. 8 is a sectional view of the system of FIG. 7.

As illustrated in FIGS. 7 and 8, the extraction cap 18 includes an outer part 31 and an inner part 33 movable with respect to the outer part. The outer part 31, which includes apertures 62 to engage the protrusions 60 of the lid, snaps onto the top 17 of the vial 14. The inner part 33 includes two ports 36, 38 for connecting the two syringes 20, 22 to the inner and outer needles (cannulas) of the extraction cannula assembly. An assembly tab 42 on the inner part 33 ensures that the larger syringe 20 can only be connected to the port that is in fluid communication with the outer extraction needle 25.

As shown in FIG. 7, a lock-out tab 44 is mounted on the large syringe 20 that forces the user to activate the large syringe first. The lock-out tab 44 blocks the plunger of syringe 22. Once syringe 20 is filled with serum extracted from vial 14, syringe 20, including lock-out tab 44, is removed and the small syringe 22 may then be activated. This ensures the proper order is followed when extracting fluid components from vial 14.

Figure 9:
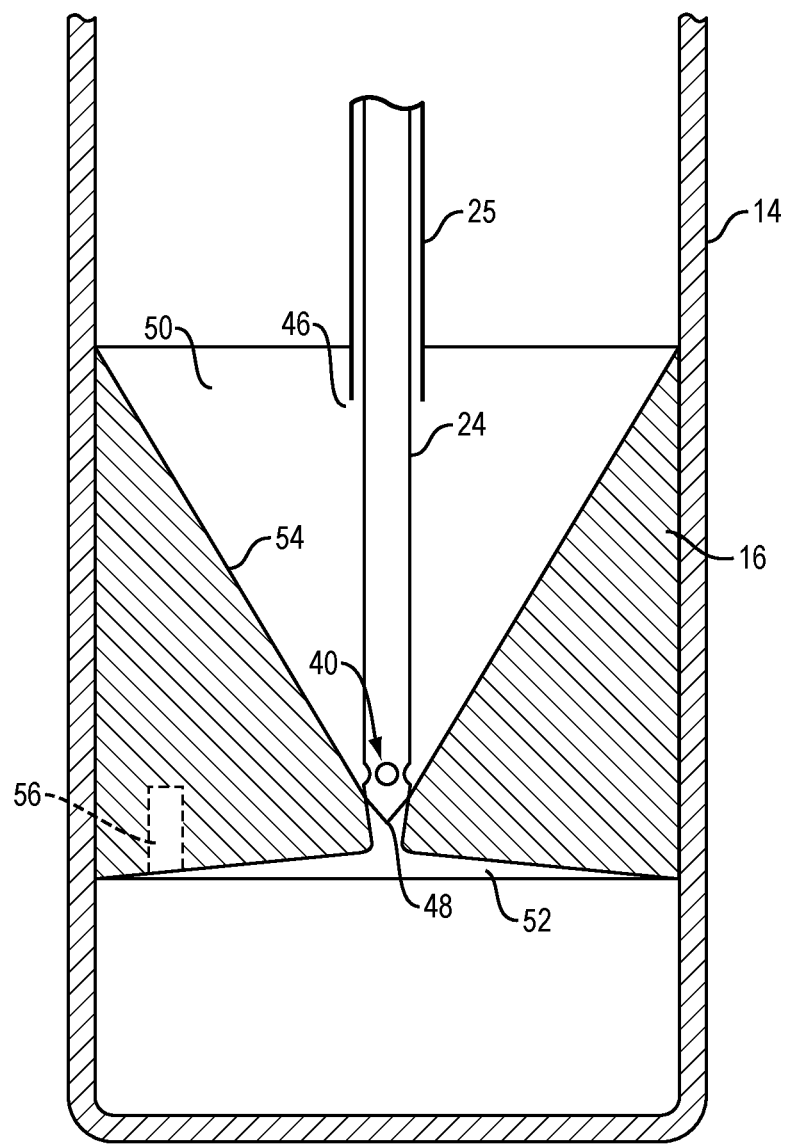
FIG. 9 illustrates a needle assembly positioned in an insert.

To remove the target cells, the extraction cap 18 is placed over the vial 14, as illustrated in FIGS. 7 and 8. The extraction needles 24, 25 are advanced through the silicone septum (container port) 30 and into the vial 14. The extraction cap 18 snaps onto the lid of the vial. Once in place, the syringe/needle assembly is pushed down by the operator so that the distal end of the needle assembly bottoms out into the funnel in the float 16 (FIG. 9). The locking screw 34 is then tightened. This screw is at an angle. As the screw is tightened, it slightly pushes the needle assembly down to ensure that it fully engages the bottom of the float. In the embodiment shown in FIGS. 7 and 8, the locking screw 34 is positioned at a small angle within the horizontal plane. In the embodiment of FIG. 3, the locking screw 34 is angled out of the horizontal plane to perform the same function.

As shown in FIGS. 8 and 9, the extraction cannula assembly includes an inner needle (inner cannula) 24 and an outer needle (outer cannula) 25. The open distal end 46 of outer needle 25 is positioned at a set distance from the distal end 48 of the inner needle 24 such that the outer needle sits at or near the top of the float 16. The outer needle is used to extract the serum (plasma). FIG. 9 illustrates the needle assembly positioned in the float (insert) 16. As shown, the inner needle 24 has a distal taper and multiple holes (ports) 40, e.g., 3 side holes, at or near its distal end 48. The inner needle 24 sits in the bottom of the float and plugs hole 52 in the float. The extraction process starts with the outer needle 25, which is in fluid communication with large syringe 20. The serum is removed until bubbles are seen in the syringe 20. Then, the selected component (e.g., stem cells, buffy coat) is removed using the small syringe 22 and the inner needle 24, the selected component being withdrawn through holes 40 of inner cannula 24. As cells of the selected component adhere to the inner wall 54 of the float (insert) 16, the cell solution that has been removed, or portion thereof, is pushed back, e.g., ejected, into the float through the holes 40 causing one or more jets of fluid in the funnel-shaped portion of the float. This jet flushing releases the cells from the float wall 54. The cells are then sucked up during a second withdrawal into the syringe 22.

Embodiments shown in FIGS. 3-9 and described herein have many advantages. One advantage of the double cannula extraction needle is that the operator only has to push the cannula assembly through the silicone septum of the separation vial once, which reduces the risk of mixing the separated fluid components in the vial. Other systems require needles or cannulae to be inserted serially, which carries a higher risk of infection and of moving the target cells to be extracted. Another advantage is the extraction needle lock, which includes a locking screw that, when tightened, drives the cannula assembly down into the float to ensure that the extraction needle (inner cannula) fully engages the bottom of the float. The locking screw of the needle lock may be positioned at an angle with respect to the extraction needle, such that rotation of the screw drives the extraction needle down. The screw may be at an angle out of the horizontal plane (FIG. 3), or at an angle within the horizontal plane, as illustrated in FIGS. 6-8. Furthermore, the lock-out tab on the larger syringe prevents an operator from using the small syringe first, thereby ensuring proper order of withdrawal of fluid components.

A system for separating components of different densities from a fluid containing cells and for concentrating cells according to another example embodiment of the invention is described below and illustrated in FIGS. 10A-17. A system for concentrating bone marrow or blood is described, although the principles of the invention can be applied to other fluids, including other physiological fluids. The system uses a container having a movable bottom, e.g., a syringe with at least one plunger, for both the collection and centrifugation of the fluid specimen.

Figure 10A:
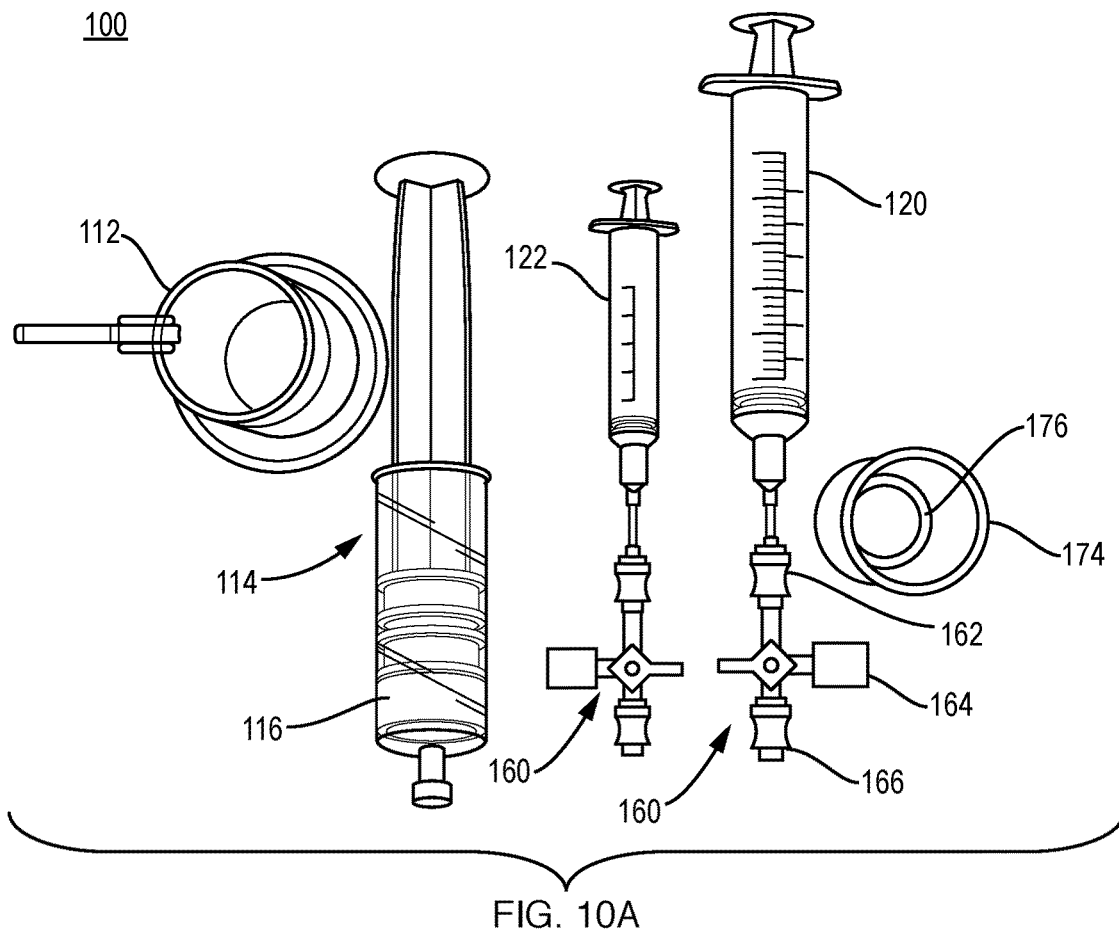
FIG. 10A illustrates a system for concentrating cells according to another example embodiment of the invention.
Figure 10B:
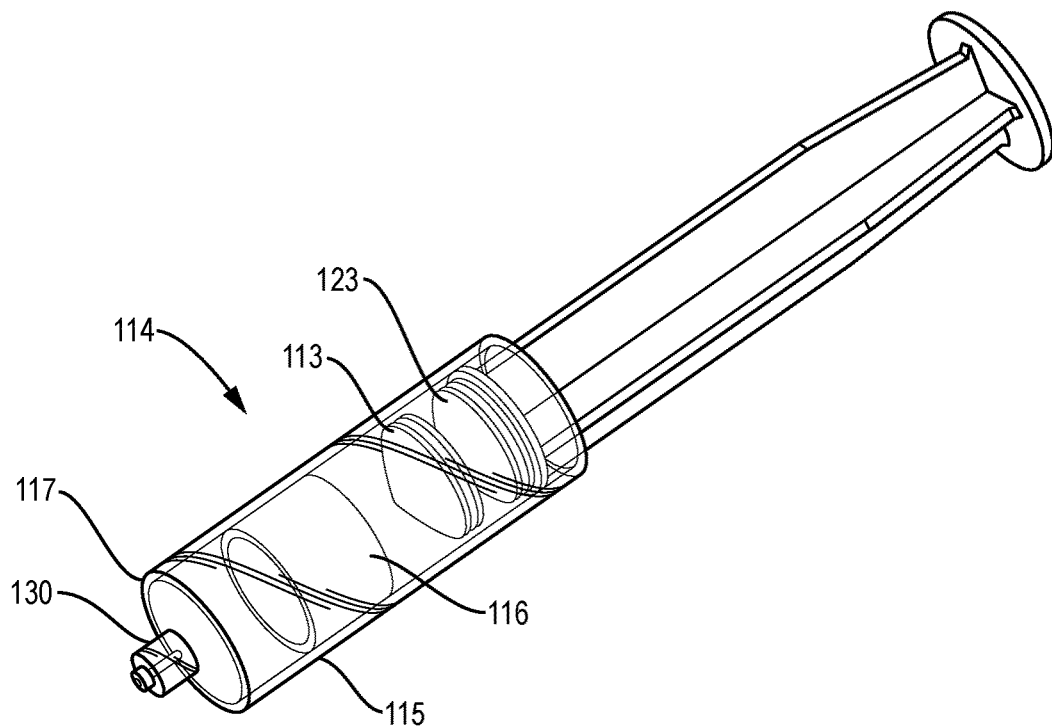
FIG. 10B is a perspective view of a double plunger syringe including an insert.

As illustrated in FIGS. 10A and 10B, a system 100 for separating components of different densities from a fluid containing cells using a centrifuge includes a collection syringe (container) 114 having a top 117, a sidewall 115 extending from the top, and a bottom 113, e.g., a plunger, disposed opposite the top and in sealing engagement with the sidewall. The container defines a cavity for receiving the fluid. An insert 116 is slidably disposed in the cavity of the container 114. Similar to insert 16 described above in reference to FIG. 9, insert 116 defines a lumen through the insert, the lumen including a hole 52 and a funnel-shaped upper portion 50 in fluid communication with the hole. The lumen forms an open fluid path between opposite ends of the insert. The insert has a density such that upon centrifugation a selected component of the fluid resides within the lumen. A container port 130, e.g., a luer connector, is disposed in the top of the container 114 to transfer the fluid into the container and to withdraw a fluid component other than the selected component from the container. As illustrated in FIG. 10A, the system further includes at least one manifold 160 that includes a manifold port 162, a vent 164 to vent the container, and a connector 166 to couple to the container port 130. A cannula 170, 172 (FIG. 14A) is receivable in the manifold port 162 and extendable through the container port 130 into the container 114 and into the lumen of the insert 116 to withdraw the selected component from the lumen or a component other than the selected component.

As illustrated in FIG. 10A, the system can include a clamping mechanism 112 that can also double as a syringe holder. The container of the system can be a syringe that includes a plunger having a removable handle (not shown) or a syringe 114 with two plungers as shown, plunger 123 having a handle and plunger 113 being without a handle. A 30 ml plasma extraction syringe 120 is connected to a cannula 170 that fits through upper injection port 162, manifold 160 and lower luer connection 166. A 5 ml concentrate extraction syringe 122 is connected to a cannula 172 that fits through upper injection port 162, manifold 160 and lower luer connection 166. The system can include a syringe holder 174 with washer on bottom and, optionally, O-ring 176. For convenience of the user, the system can include two manifolds 160, as illustrated in FIG. 10A. One manifold 160 receives cannula 170; the other manifold receives cannula 172. A standard 4-way manifold may be used for each manifold 160. The standard manifold includes 3 fluid channels and a switch (e.g, valve) 168. Using switch 168, each of the fluid channels can be selective closed or all channels can be open. Here, all channels are open. Vent 164 Coupled to the manifold can be a vent that has a micron filter. This way, a sterile environment can be maintained while venting during the extraction of fluid. The injection port 162 and the connector 166 can be swabable luer ports, which can be swabbed or wiped, e.g., with alcohol, for good sterile procedure. The swabable luer ports typically include an elastomeric (e.g., rubber) membrane that includes a slit that is normally closed, but parts when a cannula or male luer connector is inserted. Such ports are beneficial when connections are to be air tight.

Figure 11A:
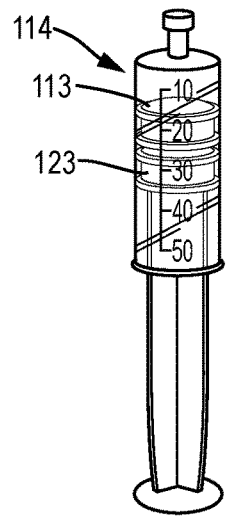
FIGS. 11A-11C illustrate movement of the plungers of the double plunger syringe of FIG. 10A.
Figure 11B:
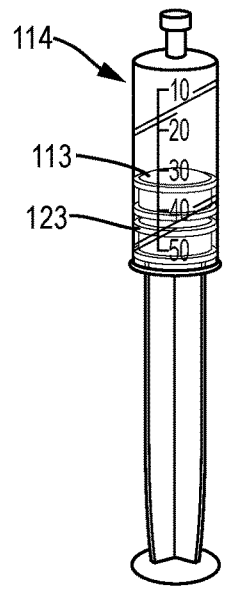
Figure 11C:
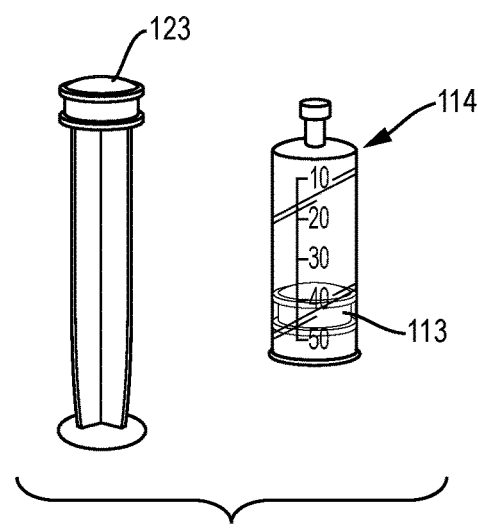

A step by step overview of the operation of the system will be described. The first step is to use the double plunger syringe 114 (alternatively, a syringe with a removable handle) to fill the syringe with the blood or marrow specimen to be concentrated. FIGS. 11A-11C illustrate movement of the plungers of the double plunger syringe 114, such as during filling of the syringe with physiological fluid. It should be noted that during filling, the syringe port 130 is coupled to another container containing the source tissue or to a tissue aspiration needle (not shown). Pulling back on the second plunger 123 via its handle forces the first plunger 113 under vacuum pressure to move back and the syringe is thus filled. The second plunger 123 can be completely removed from the barrel of syringe 114 leaving behind the first plunger 113 that is not connected to a handle. The shortened profile of the syringe with the second plunger 123 removed (or the handle removed, in case of a plunger having a removable handle) fits into commonly used centrifuges.

The second step is to connect to the syringe 114 containing the specimen (e.g., fluid tissue), after the second plunger has been removed, a small micron vented luer cap 178 and then place the syringe inside the syringe tube holder 174. The holder 174 has a solid bottom and also has an O-ring 176 attached to the solid bottom (FIG. 10A). The O-ring lines up with the seal the plunger 113 makes with the outer wall 115 of the syringe barrel. Under high g-force, this O-ring serves to prevent any leaking from the syringe into the syringe tube holder 174. G-force from the centrifuge causes the plunger to press against the O-ring on the bottom of the syringe tube holder.

Figure 12:
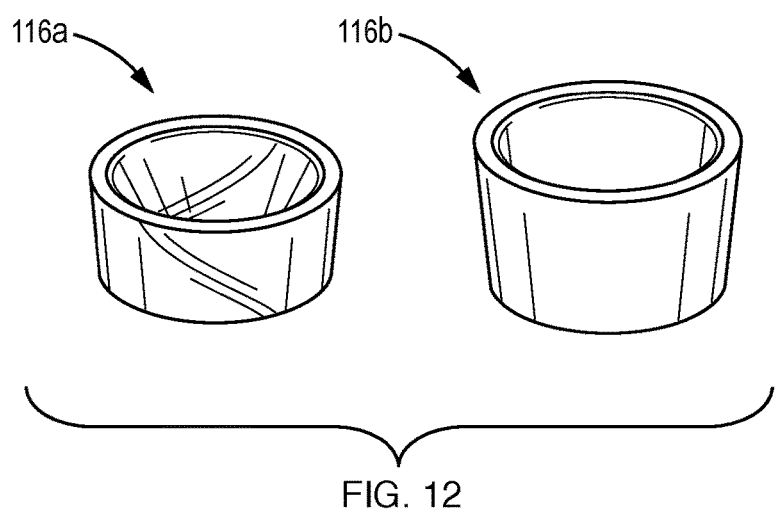
FIG. 12 illustrates inserts for use with a system for concentrating cells according to example embodiments of the invention.

Inside of the syringe 114 is a funnel shaped insert 116 (also referred to herein as a funnel) with a hole in the center. The density of the funnel is such that after density separation, target cells from blood or marrow will reside inside of the funnel. Consequently, after density separation of blood or marrow, plasma will reside at the top of the syringe 114 nearest the luer tip (container port) 130, the target cells will reside inside of the funnel 116, and red blood cells will reside beneath the funnel nearest the plunger 113. Two example funnels 116a, 116b are shown in FIG. 12.

With respect to the materials used to make the funnel 116 and the shape of the funnel, it should be noted that various materials and shapes can work. When selecting a material, one consideration is whether the funnel 116 is to be molded or machined. In FIG. 12, the funnel 116a to the left is made of REXOLITE. This material has a density of 1.05 and is easy to machine. Alternatively, a plastic material may be used, such as ABS by Dow Chemical (part #3105 FP EP) that has a density of 1.05 and is ideal for molding applications. A material that has a lower density than desired can have its density increased by adding screws or other material to the body of the funnel, as described above in reference to insert 16 of FIG. 9. Thus, various materials and plastics can be combined to fine tune the density of the funnel. For example, the funnel may be made of two parts or two different plastics. With respect to the shape of the funnel, many different shaped funnels will work. For example, a deeper, taller funnel, such as funnel 116b pictured to the right in FIG. 12, or a shallow, shorter funnel, such as the clear REXOLITE funnel 116a illustrated to the left, can be used in embodiments of the invention. Additionally, a bowl-shaped funnel or a funnel that has an inflection point, such that the angle of the wall is steeper at the bottom compared to the top, are all possible funnel shaped inserts that can be used in embodiments of the invention. Regardless of the shape, the funnel 116 has an upper funnel shaped portion 50 and a through hole 52 at the bottom as illustrated with respect to insert 16 (FIG. 9).

Figure 13:
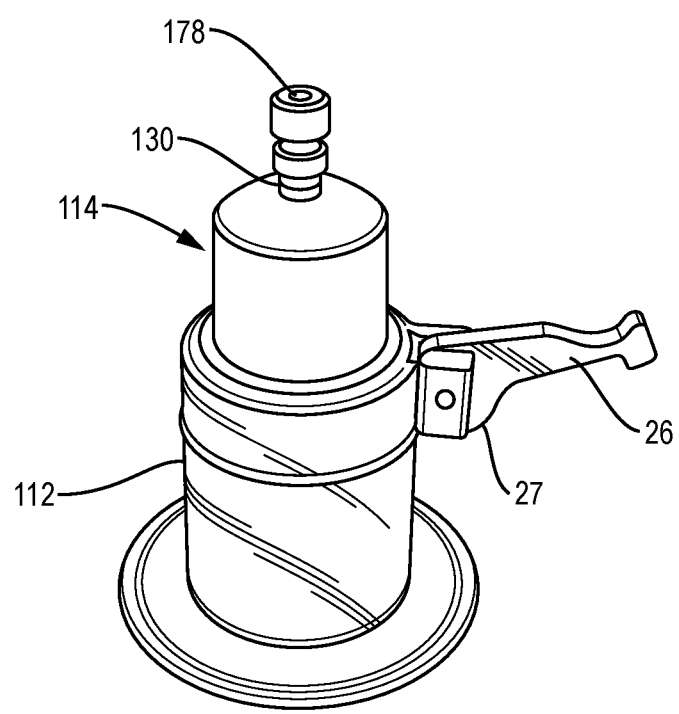
FIG. 13 illustrates the collection syringe of FIG. 11 positioned in a holder including a clamping mechanism.

The third step is to take the syringe 114 and tube holder 174 from the centrifuge, place the syringe inside the clamping mechanism 112 and engage the clamp as illustrated in FIG. 13. The pressure from the clamp will pinch the walls 115 of the syringe 114 so that the inner wall of the syringe barrel presses against the funnel 116. This pressure will freeze (i.e., lock) the funnel in place. As shown, the clamping mechanism can include a lever 26 and cam 27 similar to the clamping mechanism described above in reference to FIGS. 5, 7 and 8.

The fourth step is to remove the vented cap 178 from the collection syringe 114 and connect to the collection syringe, via the upper luer connection 130, the 30 ml plasma extraction syringe 120 connected to cannula 170 via manifold 160, as shown in FIG. 14A. Cannula 170 fits through an upper injection port 162 connected to manifold 160 as shown in FIG. 14B. Also connected to manifold 162 are a side air vent 164 and a lower luer connection 166. Thus, the collection syringe 114 is not vented during loading of the specimen but is vented, using manifold 160, during extraction of the plasma and the target fraction inside the funnel.

Figure 15:
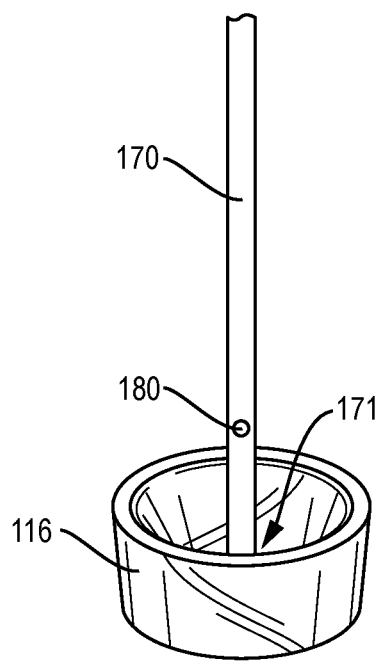
FIG. 15 illustrates a cannula positioned against an insert, the cannula including a side port displaced from the distal end of the cannula to withdraw fluid at a predetermined height above the distal end, e.g., above the insert, to withdraw substantially only plasma.

After connection the plasma extraction syringe 120 and cannula 170 to the collection syringe 114, the user pushes the extraction cannula 170 into the collection syringe. The cannula will advance until it hits the funnel 116 that has been frozen in place by the clamping mechanism 112. As illustrated in FIG. 15, cannula 170 has a blunt closed end 171 and a hole 180 a certain distance above along its shaft. This hole is positioned to be high enough to extract only the plasma above but not the contents of the funnel 116. Once the plasma is removed, the plasma extraction cannula 170 is removed from the collection syringe 114 and the plasma extraction syringe 120 is disconnected from the manifold 160. Optionally, the syringe 120 and the manifold 160 are disconnected from the luer fitting 130 of the collection syringe and removed.

Figure 16:
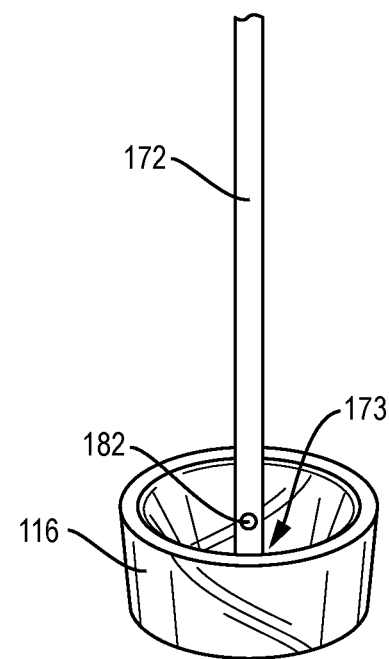
FIG. 16 illustrates a cannula positioned against an insert, the cannula including a side port displaced from the distal end of the cannula to withdraw fluid at a predetermined height above the distal end, e.g., within the insert, to withdraw substantially all of the target fraction.

Once plasma is removed from container 114, the same procedure as described above for syringe 120 and cannula 170 is repeated with the 5 ml concentrate extraction syringe 122 and cannula 172. FIG. 16 illustrates cannula 172 positioned against funnel (insert) 116, the cannula including a side port 182 displaced from the distal end 173 of the cannula to withdraw fluid at a predetermined height above the distal end, e.g., within the funnel 116, to withdraw substantially all of the target fraction. Extraction cannula 172 works the same way as the 30 ml extraction cannula except that hole (side port) 182 positioned near the cannula's blunt distal end 173 is close to the bottom of the funnel 116 so that the contents of the funnel are removed through hole 182 when vacuum pressure is applied via syringe 122. Optionally, jet flushing, described above in reference to cannula 24 of FIG. 9, may be employed by ejecting fluid through hole 182 into the funnel 116 to release cells that adhere to the funnel inner surface.

Thus, in the examples illustrated in FIGS. 15 and 16, each cannula 170, 172 includes a closed end 171, 173 to close the hole 52 in the insert 116 and at least one side port 180, 182 to withdraw a component of the fluid, be it the selected component, e.g., buffy coat, or a component other than the selected component, e.g., plasma. Each cannula 170, 172 and the insert 116 may form a seal when the closed end of the cannula closes off the hole in the insert.

Additional features of the above embodiment, as illustrated in FIGS. 10A-16, are as follows:
  a) The collection syringe (container) 114 is centrifuged 'luer tip up' and an O-ring or gasket is used to keep the syringe liquid-tight during centrifugation. If a syringe is centrifuged with the luer tip facing up, no cap or a vented cap for the luer tip should be used; otherwise the syringe distorts and leaks.

b) The use of luer connectors, injection ports, vented caps and a manifold 160 as a means to both 1) vent the collection syringe (container) and 2) insert a cannula into the syringe through the luer tip to extract fluid.

The collection syringe 114 is vented and fluid removed by employing the following novel features (see, e.g., FIGS. 14A-14B):

a) The connection between the extraction cannulas 120, 122 and the extraction syringes 170, 172 is air tight.
b) The seal around the upper injection port 162 and the cannula (170, 172) that has pierced it is also air tight.
c) The column of the manifold 160 is air tight with the exception of the air vent 164 at right angle to the syringes.
d) The connection 166 to the collection syringe 114 is air tight.

The collection syringe 114 is vented during the retrieval of the one or more target fractions. A target fraction is removed via a cannula using the negative pressure of an extraction syringe. The air vent 164 that used to accomplish this is not part of either syringe but is connected to both syringes, e.g., via the manifold 160. The luer tip 130 of the collection syringe 114 is used as the extraction port.

An alternative extraction process using a syringe PRP (Platelet Rich Plasma) system will be described. In the embodiment described above, e.g., in reference to FIG. 13, the third step in the separation procedure is to take the syringe 114 and tube holder 174 from the centrifuge and place it inside of the clamping mechanism 112 to engage the clamp and freeze the funnel 116 in place. In the alternative embodiment described below, the clamping mechanism is not used.

Figure 17:
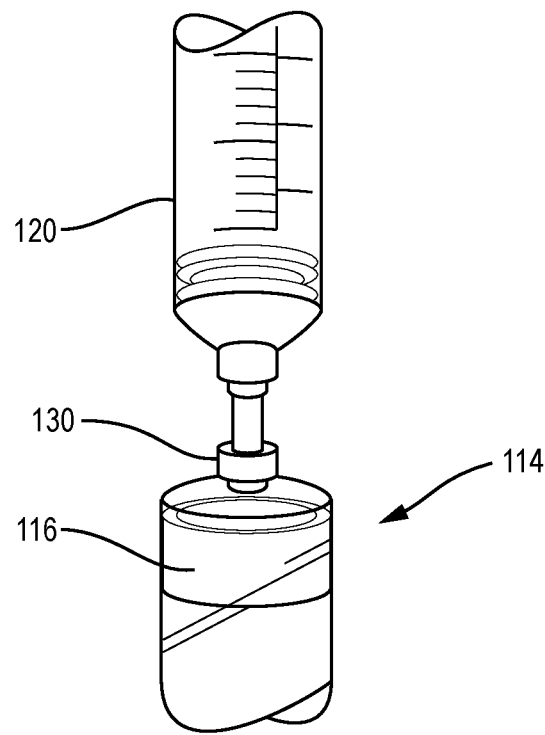
FIG. 17 illustrates an alternative embodiment including an extraction syringe coupled to a collection syringe for withdrawing a fluid component other than a selected component, e.g. for withdrawing plasma.

An alternative to removing the plasma with a cannula after clamping the funnel 116 in place is to attach a syringe 120 to the upper luer 130 of collection syringe 114 using a standard fem/fem luer connection and remove the plasma directly, without a cannula, by using the vacuum pressure of the two connected syringes (FIG. 17). Since a standard luer connection is contemplated, the plasma can be removed under vacuum pressure by pulling back on the plunger of the plasma extraction syringe 120. Thus, as the plasma is removed, the plunger 113 rises and the funnel 116 inside the barrel of the collection syringe 114 also rises. It is contemplated that the user removes the plasma until the funnel 116 reaches the top of the syringe 114. After retrieving the plasma this way, the next step is to remove the plasma extraction syringe 120 from the collection syringe 114 and connect to the collection syringe, via the upper luer connection 130, a vented 5 ml PRP extraction syringe, e.g., syringe 172 coupled to manifold 160.

The target cells will not re-mix because the walls of the funnel 116 prevent fluid turbulance or interference from the inner wall of the syringe barrel. In addition, the center hole of the funnel 116 is sized such that at 1G force, surface tension prevents fluid passage from below the funnel into the funnel. The PRP extraction syringe 122 is connected to a cannula 172 that fits through an upper injection port 162, connected to a manifold 116 that has a side air vent 164 and a lower luer connection 166. The cannula 172 can be shorter for this extraction process as the float 116 is at the top of the collection syringe 114. Thus, the collection syringe 114 is not vented during loading of the specimen but is vented during extraction the target fraction inside the funnel.

After removal of the plasma and after the PRP extraction syringe 122 and cannula 172 are connected to the collection syringe 114, the user pushes the extraction cannula 172 into the collection syringe. Since the insert 116 ends at the top of the syringe in this embodiment, the cannula 172 can be a set length, such that the cannula will advance the proper distance until it is approximately at the bottom of the funnel 116. As described above in reference to FIG. 16, this cannula has a blunt closed end to butt against the funnel 116, and a hole (e.g., a port) positioned a certain distance above the blunt end. Typically, the hole is positioned such that it ends up close to the bottom of the funnel when the blunt end of the cannula butts against the funnel. This ensures that the contents of the funnel 116 can be removed through the cannula 172 with the PRP extraction syringe 122.

Figure 2A:
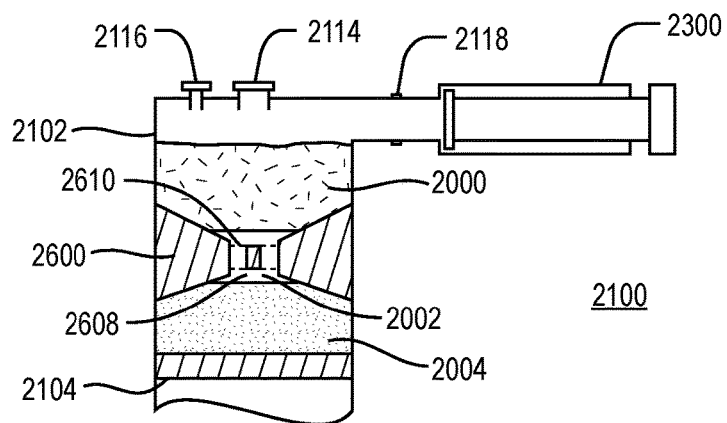
FIGS. 2A-2C are a series of sequential diagrams illustrating the extraction of fluid components using a separation system having a movable bottom.
Figure 2B:
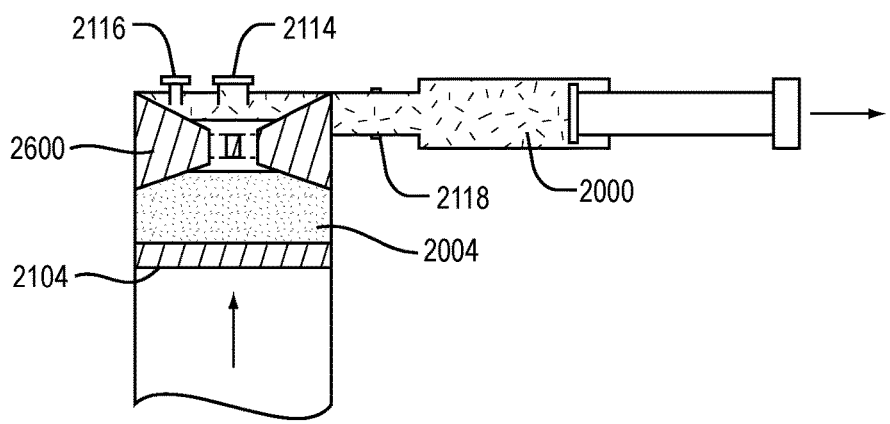
Figure 2C:
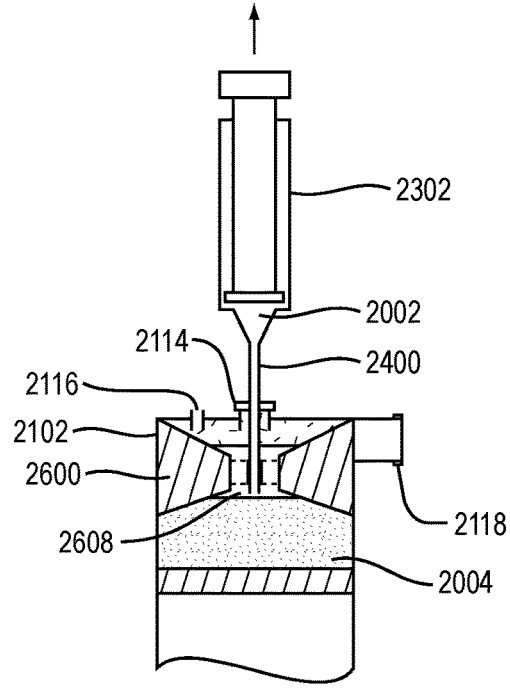

Returning to FIGS. 1 and 2, these figures illustrate embodiments described in previously filed application PCT/US20101036696, which are useful to separate cells of a different fraction of a physiological fluid using centrifugation. The embodiments each include a collection tube or container that contains a funnel (e.g., an insert or float having a funnel-shaped portion) with a through hole in the funnel. The tube is designed to accept fluid, specifically blood or marrow. The funnel has a density such that after centrifugation, cells are captured inside the funnel. Two of the methods described for removing the cells contained inside the funnel after centrifugation are summarized below.

Method 1: The first method involves the following procedures:

a) After centrifugation, pinch the funnel in place by applying a clamp on the outside of the tube (e.g., container having a fixed bottom). The pressure on the tube causes the tube to flex. This then causes the inside wall of the tube to pinch against the outside wall of the funnel.
b) Once the funnel is secured in place, a double needle apparatus (inner cannula within outer cannula) is inserted through a center port. The blunt tip of the needle mates with the center hole of the funnel blocking off fluid below the funnel from fluid above the funnel.
c) The upper access hole (side port) of the double needle extracts all fluid that resides above the top of the funnel
d) The lower access hole (side port) of the double needle extracts all fluid that resides inside the funnel.

Method 2: The second method involves the following procedure:

a) The fluid is loaded into a syringe (e.g., a container having a movable bottom or plunger) containing the funnel; the syringe can have no plunger handle or can have a removable plunger handle
b) The syringe has a center luer connection and a side luer connection, both of which are closed.
c) In one example, the center luer connection on the underside, inside the barrel of the syringe, has connected to it a blunt needle with side ports
d) After centrifugation, the target cells reside inside the funnel
e) Upper fluid (plasma) is removed via a plasma-syringe through the side luer connection. Because the system is a syringe, it is under vacuum pressure; consequently, as fluid is removed, the funnel and plunger move up.
f) Once the majority of the fluid has been removed, the blunt end of the needle meets the center hole of the rising float (funnel) and effectively seals all fluid above the float from fluid below the float. The port retrieving the plasma also mates with the float simultaneously so that no further fluid can be removed from the side port once the blunt needle impales the rising float.

g) The plasma syringe is removed and a vented cap added which now makes the system not under vacuum pressure.

h) Another syringe is connected to the center port and the target cells are removed.

Thus, of the two methods for removing the target cells from the funnel described above, the first involves freezing (e.g., clamping) the float in place and moving the needle assembly into the funnel to get the cells, while the second method involves using the vacuum pressure from the syringe to move the funnel up so that it impales itself into the fixed blunt needle assembly under the cap of the syringe. Please refer to WO 2010/138895 A2, e.g., FIGS. 13-33 and associated text, for a more complete description of the two methods described above.

Figure 18:
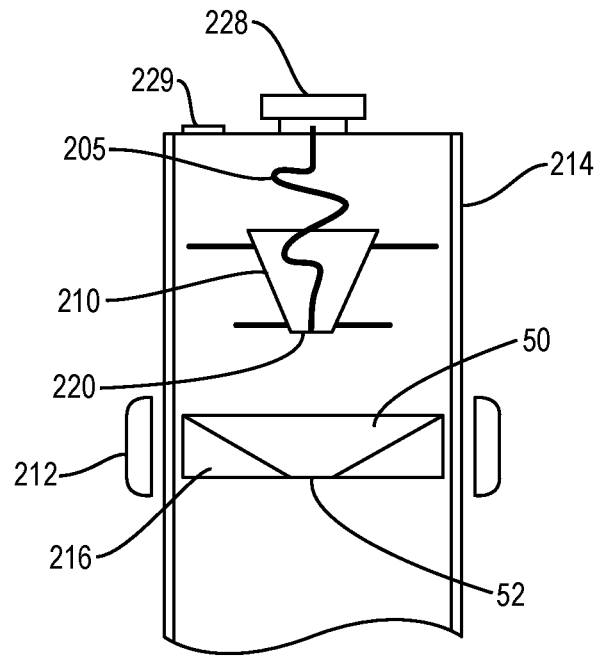
FIG. 18 illustrates a separation system according to another example embodiment of the invention.
Figure 19:
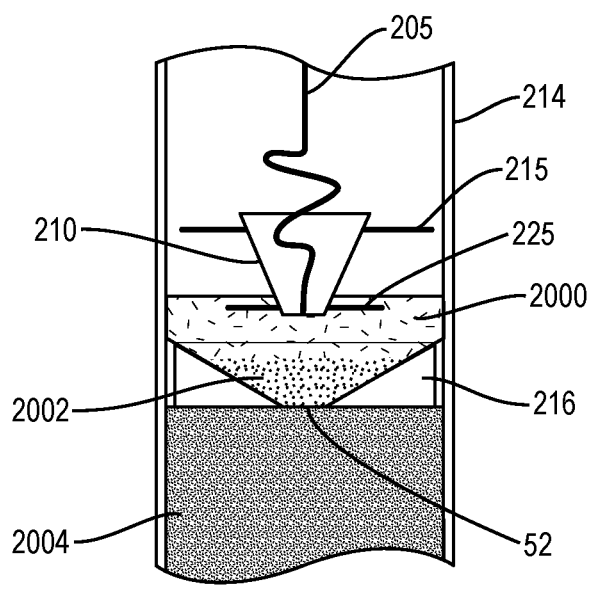
FIG. 19 illustrates the separation system of FIG. 18 showing different components of a fluid after centrifugation.

Described below in reference to FIGS. 18 and 19 is yet another apparatus and associated method for extracting cells from the collection funnel of a separation system. The apparatus and method include an upper and a lower funnel that are disposed inside the collection tube (container). As illustrated in FIG. 18, blood is loaded into a tube (container) 214 that defines a cavity that serves as the collection chamber for fluid. The tube 214 has an injection port 228 and an air vent 229. Inside the collection tube 214 and in fluid communication with the injection port 228 is a flexible, optionally, clear tube 205 that is attached to a funnel 210 (referred to as the first or upper funnel) also disposed in the container 214. The density of the upper funnel 210 is less than blood plasma. For example, the density of the upper funnel can be about 1.0.

After centrifugation, the bulk of the upper funnel 210 is floating above the plasma 2000, as illustrated in FIG. 19. The bottom point of the upper funnel 210 has sunk slightly into the plasma or is in contact with the plasma. As shown, the funnel 210 is narrower than the diameter of the collection tube 214. The funnel 210 has stabilization fins 215 at the top that extend from the funnel to approximately the sidewall of the tube 214 without touching the tube. These fins 215 are placed in such a manner that the upper funnel 210 remains oriented vertically with respect to the collection tube. The flexible tube 205 is attached at one end to the portion of the upper funnel where through hole 220 is located in the funnel. The other end of the tube 205 is connected to the port 228 in the top (e.g., cap) of the collection tube 214. Tube 205 can be a small diameter clear tube that can flex and curl in on itself. Fluid is added to the collection tube 214 through the port 228 with a syringe. The fluid then travels through the length of flexible tube 205 and exits through hole 220 in the upper funnel 210 into the hollow chamber of collection tube 214. Fluid is removed from the chamber through the same path.

Beneath the upper funnel 210 is a second funnel 216 that has a density of about 1.06, which is a higher density than the upper funnel and which allows the lower funnel 216 to float at the intermediate zone between red cells 2004 and plasma 2000. After centrifugation, most of the platelets and white cells from blood or marrow reside within the lower funnel, as illustrated in FIG. 19. The lower funnel 216 has a through hole 52, similar to other funnel shaped inserts described herein. Because the funnel 216 is open at the top and the bottom, it results in cleaner fluid flow and cleaner separation of components of the fluid, e.g., red cells, plasma, and target cells in the intermediate layer 2002 between red cells and plasma.

After centrifugation, the user can attach a syringe to the upper port 228 and begin to retrieve plasma first. The upper funnel 210 sinks as fluid in the chamber of tube 214 is removed but initially remains floating on the top of the fluid. After the desired amount of plasma has been removed, the user can switch syringes and begin to remove the remaining fluid above the lower funnel 216 and the contents of what is inside the lower funnel.

As additional fluid is removed, the upper funnel 210 continues to sink until it hits the lower funnel 216. The angle of the upper funnel 210 is steeper than the angle of the lower funnel 216 so that the upper funnel fits into the lower funnel. The upper funnel 210 can have bottom stabilization fins 225, so that the point of the upper funnel stops a certain distance below the bottom of the lower funnel 216. This can also be accomplished by making the upper funnel 210 a certain height so that the upper stabilization fins 215 contact the upper surface of the lower funnel 216. Additionally, a clamp 212 can be added after centrifugation that pinches the sidewall of the collection tube, such that the sidewall deforms and pinches against an outer surface of the lower funnel. In this way, the lower funnel 216 can be clamped in place and does not move as the upper funnel 210 mates with it during extraction of fluid. This allows the user to only withdraw the contents of the lower funnel 216 but not any fluid which is contained beneath the lower funnel.

As illustrated in FIG. 19, after centrifugation, red cells 2004 are below the lower funnel 216, target cells of the density desired (e.g., buffy coat) 2002 are inside the lower funnel, plasma 2000 is above the target cells, and the upper funnel 210 is floating on top of the plasma. As described above, the user first removes plasma 2000 by attaching a syringe (not shown) to the center port 228 (FIG. 18) of tube 214 and pulling back on the plunger of the syringe. This causes fluid to flow through the hole (port) 220 at the bottom of the upper funnel 210, through the flex tube 205 and into the syringe. The user can remove as much plasma as is desired. Once the desired amount of plasma is removed, the user can remove the syringe containing the plasma and attach a second syringe (not shown) and remove the remaining fluid that is contained above and inside the lower funnel 216. The stabilization fins 215, 225 and the relative height of the two funnels 210, 216 can be adjusted such that the upper funnel 210 dead ends against the lower funnel 216 so that no fluid from beneath the lower funnel is removed during the extraction process.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims. For example, the double plunger collection syringe described herein may be used to separate fluid components other than those described herein and may be used in applications other than those described herein. Further, the example manifold disclosed herein, including the luer connection ports and micron vent, may be used to transfer fluids in a sterile manner in other applications, and may be used with syringes, cannulas, and containers other than those described herein. Further, inserts other than those illustrated and described herein may be used in combination with containers, cannulas and syringes to separate components of a fluid. For example, inserts need not have a density as described herein.

What is claimed is:

1. A system for separating components of different densities from a fluid containing cells using a centrifuge, the system comprising:
   a syringe having a top, a sidewall extending from the top forming a syringe tube, and a plunger slidably disposed inside the syringe tube and in sealing engagement with the sidewall, the sidewall being substantially straight from the top to a distal end of the syringe tube, the distal end of the syringe tube including an opening, the syringe defining a cavity for receiving the fluid containing cells;
   a Luer port disposed in the top of the syringe to transfer the fluid containing cells into the syringe and to extract one or more separated layers containing cells from the syringe; and
   a syringe holder at least partially closing the opening of the distal end of the syringe tube, the syringe holder not connected to the plunger inside the syringe tube,
   the syringe and syringe holder configured for placement in a centrifuge and for exposure of the syringe and syringe holder to elevated g force in the centrifuge, the elevated g force urging the plunger toward the syringe holder, wherein the syringe holder is in physical contact with the syringe tube on the distal end and includes a surface arranged to contact the plunger at a bottom perimeter of the plunger during centrifugation, to provide support and maintain the sealing engagement of the plunger with the sidewall of the syringe tube, to prevent fluid from leaking outside the syringe.

2. The system of claim 1, wherein the plunger has a removable handle.

3. The system of claim 1, wherein the plunger is a first plunger and further including a second plunger disposed in the syringe below the first plunger to move the first plunger to load the fluid containing cells into the syringe.

4. The system of claim 3, wherein the syringe holder defines a cavity for receiving the syringe, the second plunger or a handle of the second plunger being removable prior to receiving the syringe in the syringe holder.

5. The system of claim 1, wherein the syringe holder defines a cavity for receiving the syringe, and wherein the syringe holder includes an O-ring at a bottom of the syringe holder to prevent fluid from leaking from the syringe into the syringe holder.

6. The system of claim 1, wherein the syringe includes an insert slidably disposed in the syringe tube between the plunger and the top, the insert, upon centrifugation, allowing fluid components of a density lower than a certain density to rise above the insert and fluid components of a density higher than the certain density to sink below the insert.

7. The system of claim 1, further comprising a manifold including a manifold port, a vent to vent the syringe, and a connector to couple to the Luer port.

8. The system of claim 7, further comprising a cannula receivable in the manifold port and extendable through the Luer port into the syringe to withdraw a selected component of the fluid.

9. The system of claim 8, further comprising an insert slidably disposed in the cavity and defining a lumen through the insert, the lumen including a hole and a funnel-shaped upper portion in fluid communication with the hole, the insert having a density such that upon centrifugation a selected component of the fluid resides within the lumen, the lumen forming an open fluid path between opposite ends of the insert.

10. The system of claim 9, wherein the cannula includes a closed end to close the hole in the insert and a side port to withdraw the selected component, the cannula and the insert forming a seal when the closed end of the cannula closes off the hole in the insert.

11. The system of claim 9, wherein the cannula is a first cannula, and further including a second cannula extendable through the Luer port to withdraw a component other than the selected component.

12. The system of claim 11, wherein the second cannula is receivable in the manifold port.

13. The system of claim 9, further including a clamping mechanism to hold the insert in place after centrifugation, the clamping mechanism configured to press the sidewall inward against the insert.

* * * * *